(12) United States Patent
Wisniewski et al.

(10) Patent No.: US 10,662,246 B2
(45) Date of Patent: May 26, 2020

(54) MONOCLONAL ANTIBODY TO TREAT ALZHEIMER'S DISEASE, PRION DISEASE, FRONTOTEMPORAL DEMENTIAS AND TRAUMATIC BRAIN INJURY/CHRONIC TRAUMATIC ENCEPHALOPATHY

(71) Applicant: NEW YORK UNIVERSITY, New York, NY (US)

(72) Inventors: Thomas Wisniewski, Staten Island, NY (US); Allal Boutajangout, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 16/031,418

(22) Filed: Jul. 10, 2018

(65) Prior Publication Data

US 2019/0010238 A1    Jan. 10, 2019

Related U.S. Application Data

(60) Provisional application No. 62/530,664, filed on Jul. 10, 2017.

(51) Int. Cl.
| | |
|---|---|
| *C07K 16/28* | (2006.01) |
| *C07K 16/10* | (2006.01) |
| *A61P 25/18* | (2006.01) |
| *A61P 25/28* | (2006.01) |
| *C07K 16/18* | (2006.01) |
| *A61K 39/00* | (2006.01) |

(52) U.S. Cl.
CPC .......... *C07K 16/2872* (2013.01); *A61P 25/18* (2018.01); *A61P 25/28* (2018.01); *C07K 16/1036* (2013.01); *C07K 16/18* (2013.01); *A61K 2039/505* (2013.01); *C07K 2317/24* (2013.01); *C07K 2317/34* (2013.01)

(58) Field of Classification Search
None
See application file for complete search history.

(56) References Cited

U.S. PATENT DOCUMENTS

| 8,951,519 B2 | 2/2015 | Wisniewski |
| 9,834,582 B2 | 12/2017 | Wisniewski |
| 2019/0256612 A1 | 8/2019 | Wisniewski |

OTHER PUBLICATIONS

Citron, Alzheimer's disease: strategies for disease modification.Nat Rev Drug Discov. May 2010;9(5):387-98. doi: 10.1038/nrd2896. (Year: 2011).*
(Paul, Fundamental Immunology, (textbook), 1993, pp. 292-295 (Year: 1993).*
Rudikoff et al. (Proc Natl Acad Sci USA, 1982; 79(6):1979-1983 (Year: 1982).*

(Continued)

*Primary Examiner* — Aurora M Fontainhas
(74) *Attorney, Agent, or Firm* — Pepper Hamilton LLP

(57) ABSTRACT

The present invention is directed to an anti-prion monoclonal antibody and its use for the treatment of conditions associated with or mediated by proteins or peptides having a toxic oligomeric form. These conditions include, but are not limited to, Alzheimer's disease, frontotemporal dementias, traumatic brain injury, and chronic traumatic encephalopathy.

19 Claims, 15 Drawing Sheets

Specification includes a Sequence Listing.

(56) References Cited

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*
Edwards et al., J Mol Biol. Nov. 14, 2003;334(1):103-18.The remarkable flexibility of the human antibody repertoire; isolation of over one thousand different antibodies to a single protein, BLyS. (Year: 2003).*
Kussie et al., J Immunol. Jan. 1, 1994;152(1):146-52.A single engineered amino acid substitution changes antibody fine specificity. (Year: 1994).*
Spinner et al., "CpG Oligodeoxynucleotide-Enhanced Humoral Immune Response and Production of Antibodies to Prion Protein PrPSc in Mice Immunized With 139A Scrapie-Associated Fibrils," J Leukoc. Biol 81:1374-1385 (2007).
Pankiewicz et al., "Clearance and Prevention of Prion Infection in Cell Culture by Anti-PrP Antibodies," Eur. J Neurosci 23(10):2635-2647 (2006).
Sadowski et al., "Anti-PrP Mab 6D11 Suppresses PrPSc Replication in Prion Infected Myeloid Precursor Line FDC-P1/22L and in the Lymphoreticular System In Vivo," Neurobiol Dis 34:267-278 (2009).
Chung et al., "Anti-PrPC Monoclonal Antibody Infusion as a Novel Treatment for Ab Oligomer Cognitive Cognitive Deficits," BMC Neuroscience 11:130 (2010).
Goñi et al., "Anti-β-sheet Conformation Monoclonal Reduces Tau and Aβ Oligomer Pathology in an Alzheimer's Model." Alzheimer's Research and Therapy, 10:10 (2018).

\* cited by examiner

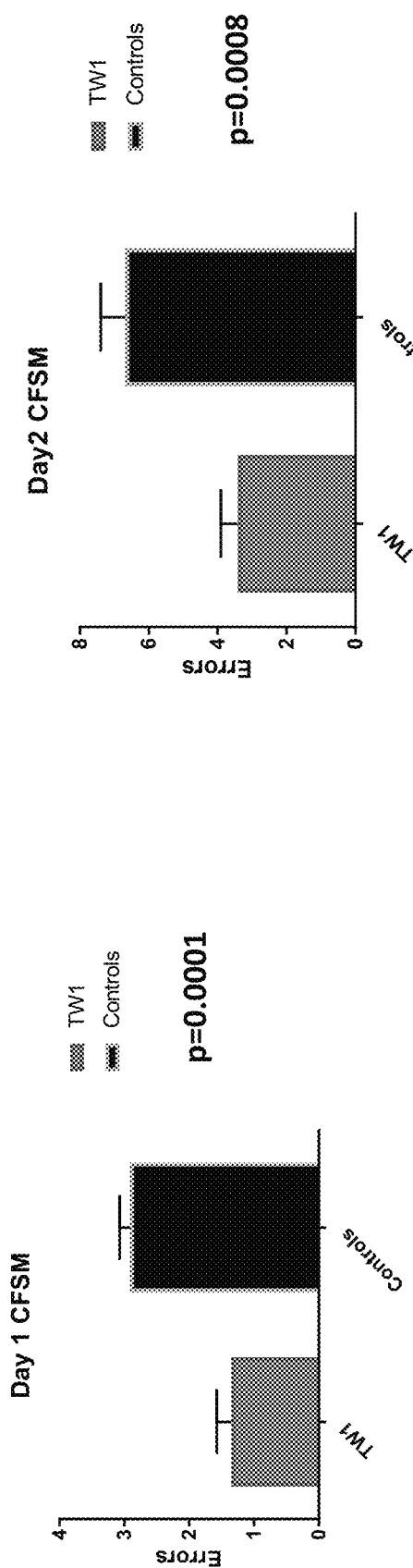
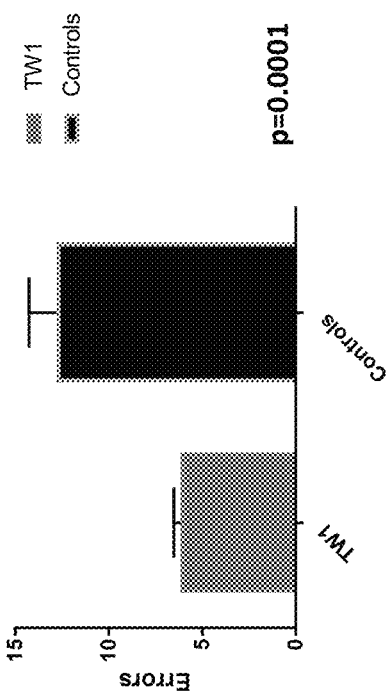
FIG. 11A
FIG. 11B
FIG. 11C

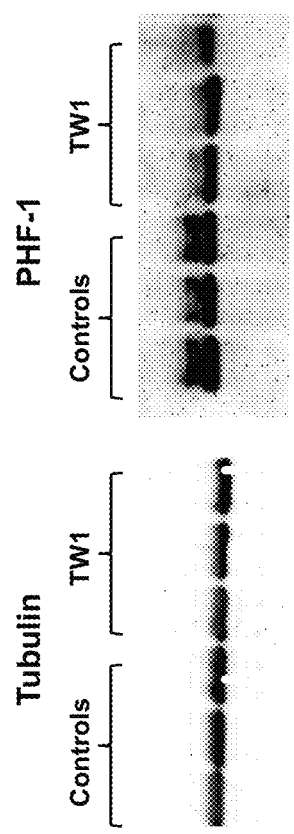
FIG. 15A
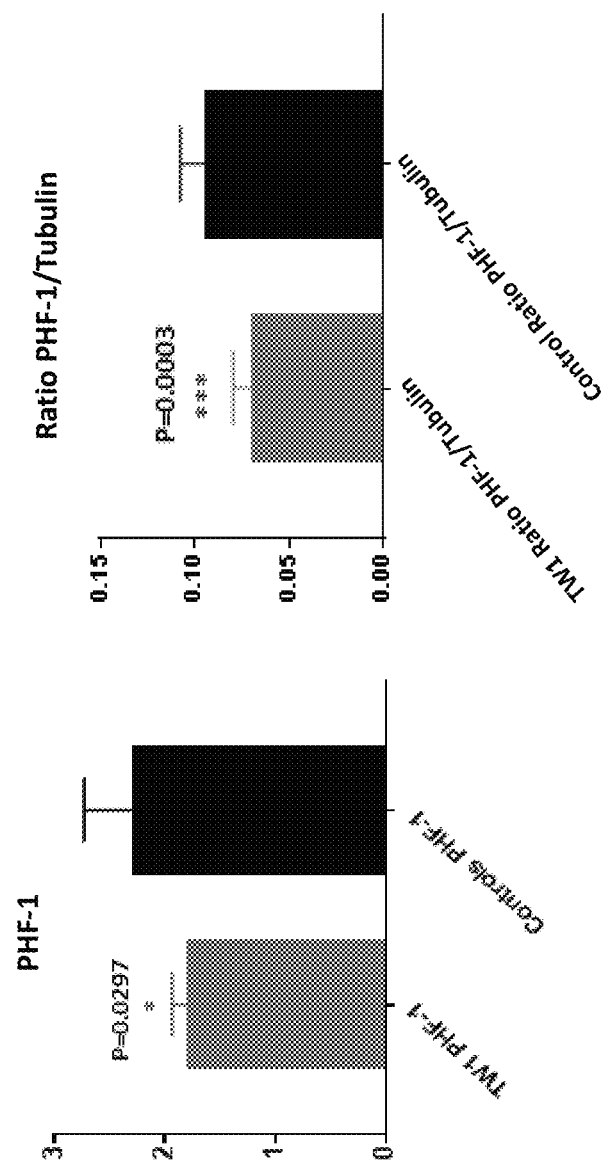
FIG. 15B
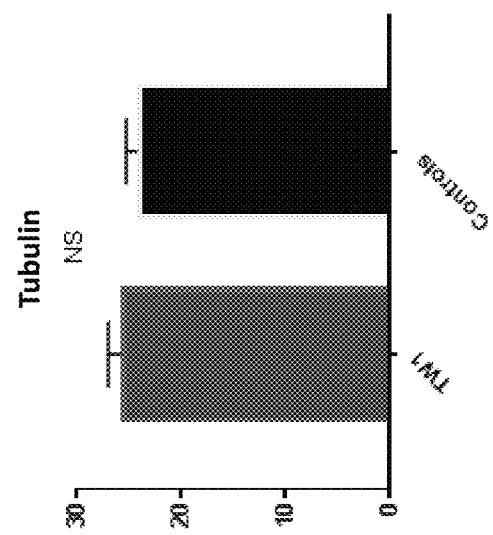

MONOCLONAL ANTIBODY TO TREAT ALZHEIMER'S DISEASE, PRION DISEASE, FRONTOTEMPORAL DEMENTIAS AND TRAUMATIC BRAIN INJURY/CHRONIC TRAUMATIC ENCEPHALOPATHY

This application claims the priority benefit of U.S. Provisional Patent Application Ser. No. 62/530,664, filed Jul. 10, 2017, which is hereby incorporated by reference in its entirety.

This invention was made with government support under NS073502 awarded by the National Institutes of Health. The government has certain rights in the invention.

FIELD OF THE INVENTION

The present invention is directed to an antibody for the treatment of conditions associated with or mediated by proteins or peptides having a toxic oligomeric form, including, but not limited to, Alzheimer's disease, frontotemporal dementias, traumatic brain injury, and chronic traumatic encephalopathy.

BACKGROUND OF THE INVENTION

Neurofibrillary tangles (NFTs), a hallmark lesion in Alzheimer's disease (AD), are composed mainly of paired helical filaments (PHF), which have a hyperphosphorylated form of the microtubule associated protein tau as the major component (Nelson et al., "Correlation of Alzheimer's Disease Neuropathologic Changes With Cognitive Status: A Review of the Literature," *JNEN* 71:362-381 (2012)). Tau hyperphosphorylation and associated aggregation/oligomerization is thought to be a critical event linked to microtubule disorganization, and the subsequent generation of neurofibrillary tangles which are associated with neuronal toxicity, dysfunction and synaptic loss (Braak et al., "Stages of the Pathologic Process in Alzheimer Disease: Age Categories From 1 to 100 Years," *J Neuropathol. Exp. Neurol* 70(11): 960-9 (2011)). Oligomeric species of tau are thought to be critical for the "prion-like" spread of pathology and for neuronal toxicity (Guo and Lee, "Cell-to-cell Transmission of Pathogenic Proteins in Neurodegenerative Diseases," *Nat Med* 20:130-138 (2014)). Numerous studies have been performed to gain a better understanding of the role of aggregated Aβ species on AD pathology; however, recently there has been much more focus on tau related pathology with the published failure of several amyloid β targeted therapeutic approaches in phase III clinical trials (Drummond and Wisniewski, "Alzheimer's Disease: Experimental Models and Reality," *Acta Neuropathol* 133:155-175 (2017)).

The present invention is directed to overcoming these and other deficiencies in the art.

SUMMARY OF THE INVENTION

A first aspect of the present disclosure is directed to an antibody or binding fragment thereof that binds prion protein, said antibody or binding fragment thereof comprising a heavy chain variable region. The heavy chain variable region comprises a complementarity-determining region 1 (H-CDR1) comprising an amino acid sequence of SEQ ID NO: 1, or a modified amino acid sequence of SEQ ID NO: 1, said modified sequence containing 1 or 2 amino acid residue modifications as compared to SEQ ID NO: 1; a complementarity-determining region 2 (H-CDR2) comprising an amino acid sequence of SEQ ID NO: 2, or a modified amino acid sequence of SEQ ID NO: 2, said modified sequence containing 1, 2, 3, or 4 amino acid residue modifications as compared to SEQ ID NO: 2; and a complementarity-determining region 3 (H-CDR3) comprising an amino acid sequence of SEQ ID NO: 3, or a modified amino acid sequence of SEQ ID NO: 3, said modified sequence containing 1, 2, or 3 amino acid residue modifications as compared to SEQ ID NO: 3.

The antibody or binding fragment thereof as described herein may further comprise a light chain variable region. The light chain variable region comprises a complementarity-determining region 1 (L-CDR1) having an amino acid sequence of SEQ ID NO: 5, or a modified amino acid sequence of SEQ ID NO: 5, said modified sequence containing 1 or 2 amino acid residue modifications as compared to SEQ ID NO: 5; a complementarity-determining region 2 (L-CDR2) having an amino acid sequence of SEQ ID NO: 6, or a modified amino acid sequence of SEQ ID NO: 6, said modified sequence containing 1 or 2 amino acid residue modifications as compared to SEQ ID NO: 6; and a complementarity-determining region 3 (L-CDR3) having an amino acid sequence of SEQ ID NO: 7, or a modified amino acid sequence of SEQ ID NO: 7, said modified sequence containing 1 or 2 amino acid residue modifications as compared to SEQ ID NO: 7.

Another aspect of the present disclosure is directed to a method of inhibiting a protein or peptide in a toxic oligomeric form from interacting with prion protein ($PrP^c$) in a subject. This method involves administering to the subject a pharmaceutical composition comprising the anti-PrP antibody or binding fragment thereof of the present disclosure in an amount effective to inhibit the protein or peptide in its toxic oligomeric form from interacting with $PrP^c$ in the subject.

Another aspect of the present disclosure is directed to a method of inhibiting onset of one or more symptoms of a condition mediated by a protein or peptide in a toxic oligomeric form in a subject. This method involves administering to the subject a pharmaceutical composition comprising the anti-PrP antibody or binding fragment thereof of the present disclosure in an amount effective to prophylactically inhibit onset of one or more symptoms of the condition mediated by the protein or peptide in its toxic oligomeric form the subject.

Another aspect of the present disclosure is directed to a method of treating a condition mediated by a protein or peptide in a toxic oligomeric form in a subject. This method involves administering to the subject a pharmaceutical composition comprising the anti-PrP antibody or binding fragment thereof of the present disclosure in an amount effective to treat the condition mediated by the protein or peptide in its toxic oligomeric form in the subject.

BRIEF DESCRIPTION OF THE DRAWINGS

FIGS. 1A and 1B show tau pathology using anti-PHF1 immunolabeling in dentate gyrus (top left) and CA1 (top right) sections, respectively, taken from a hTau transgenic mouse model at 2.5 months. FIGS. 1C and 1D show tau pathology using anti-PHF1 immunolabeling in dentate gyrus (bottom left) and CA1 (bottom right) sections, respectively, in the hTau/PS1 transgenic mouse model at ~2 months.

Figures 2A, 2B, 2C:
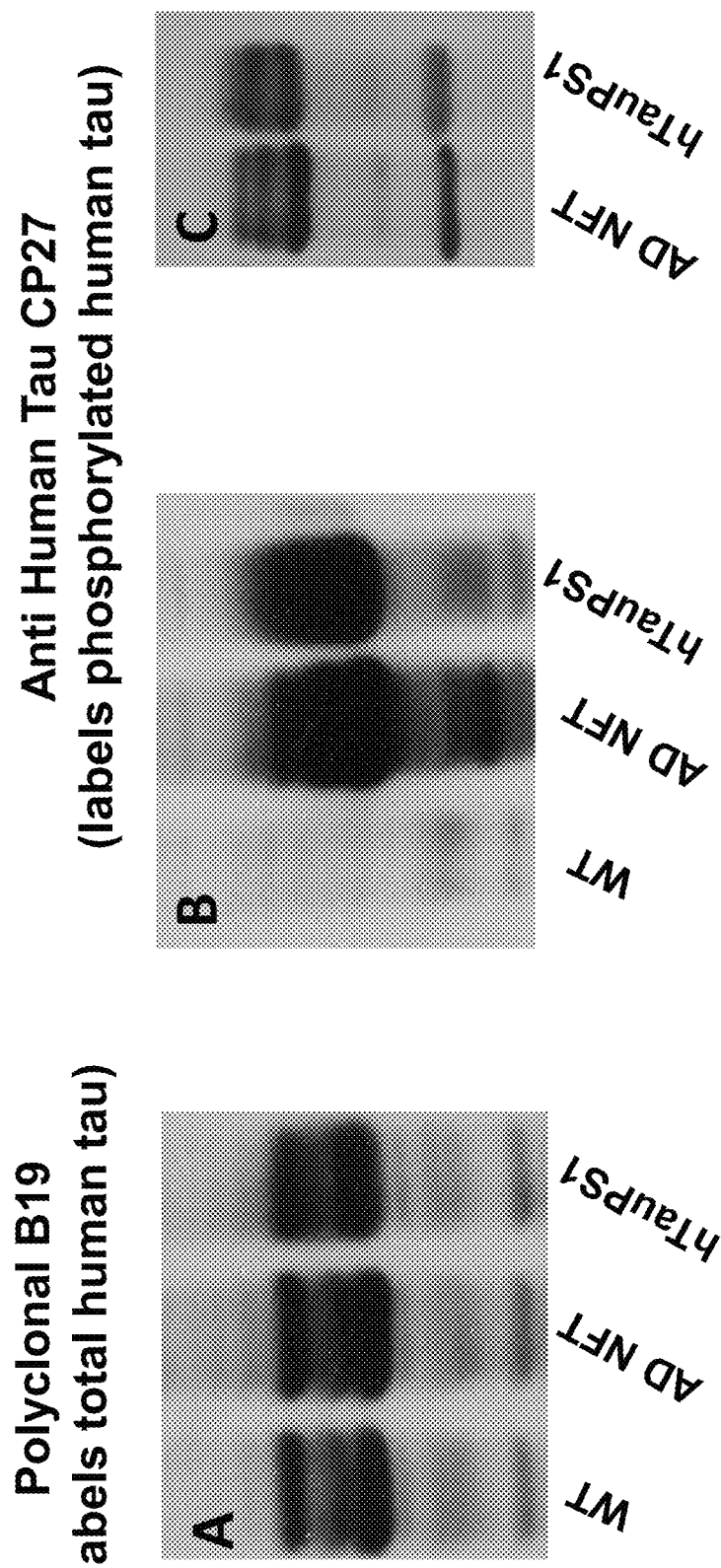
FIGS. 2A-2C are western blots showing tau immunoreactivity in brain extracts from 8 month old hTau/PS1 mice.

Total tau was detected using the polyclonal B19 antibody (FIG. 2A) and hyperphosphorylated tau was detected with anti-Tau CP27 antibody (FIGS. 2A and 2C). The biochemical characterization of hyperphosphorylated tau in hTau/PS1 Tg mice is very similar to AD neurofibrillary tangles (AD-NFT), which was included in each blot for comparison.

Figure 3:
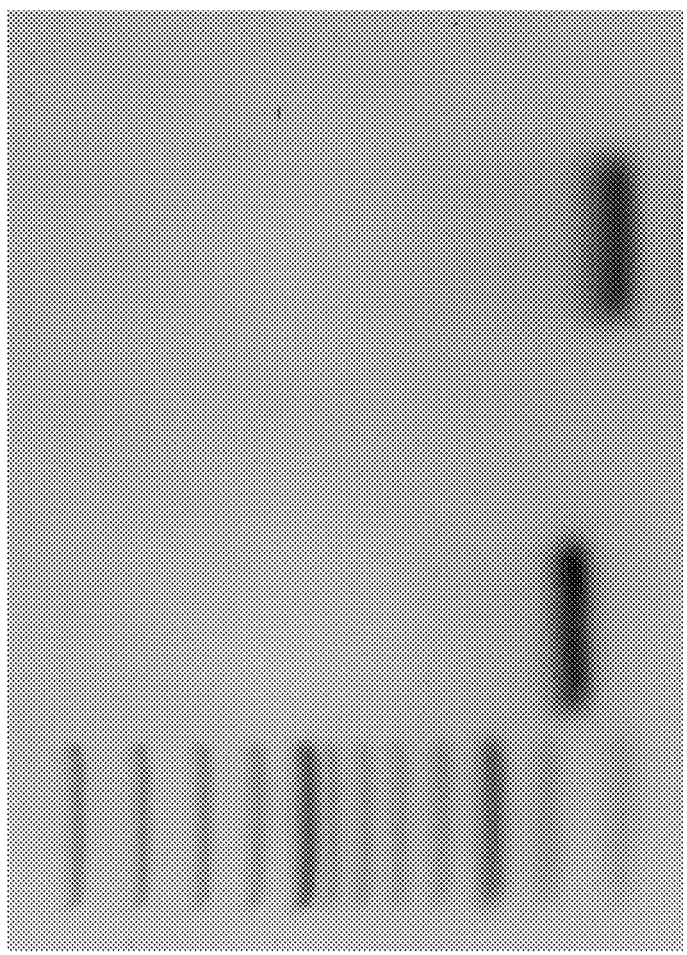

FIG. 3 show the purification of the cDNA of the variable heavy ($V_H$) (lane 2) and variable light ($V_L$) (lane 4) regions of the anti-PrP antibody described herein.

Figure 4:
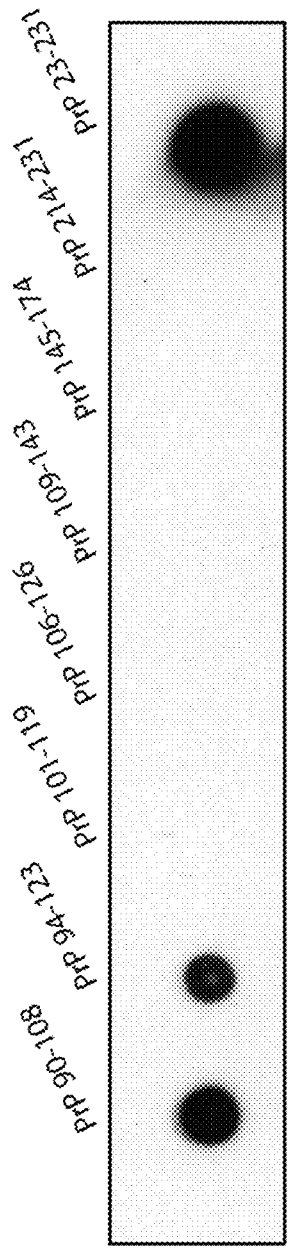

FIG. 4 is a dot blot showing epitope mapping of the anti-PrP antibody described herein to an epitope of human PrP that includes or comprises residues 94-108 of the protein (SEQ ID NO: 9).

Figure 5:
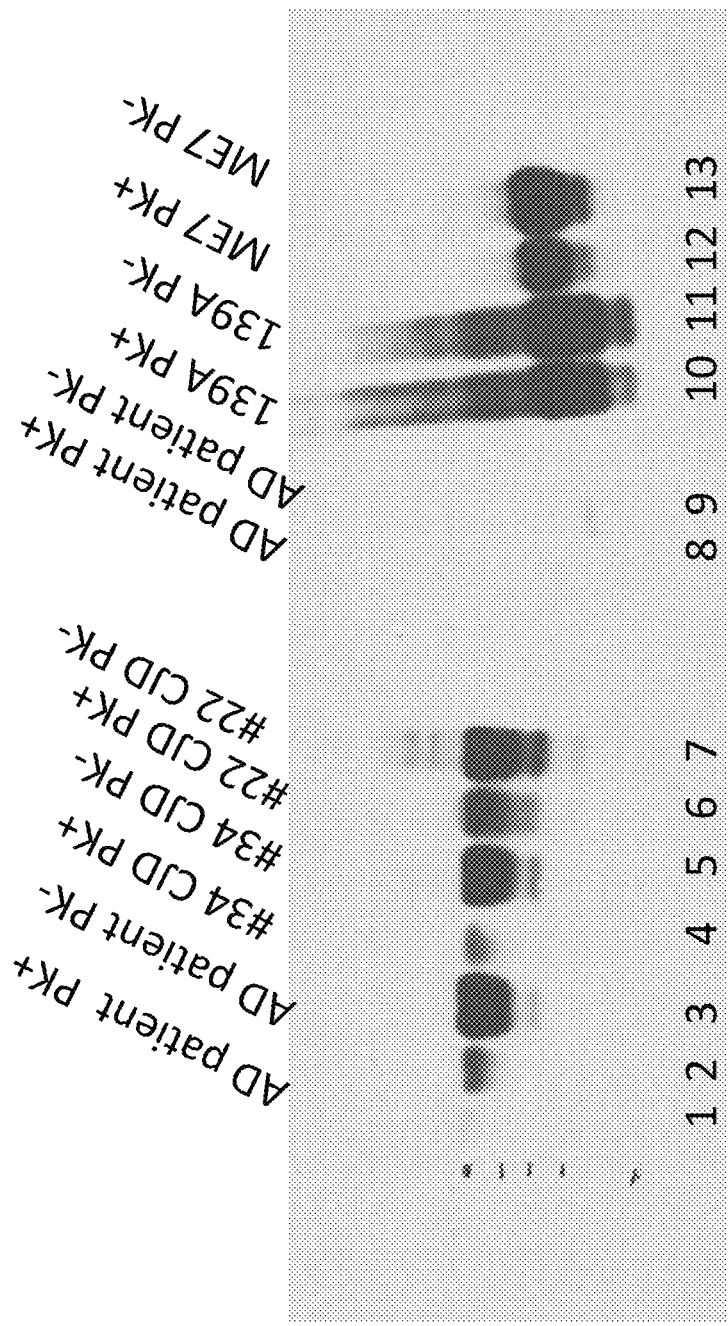

FIG. 5 is a western blot showing the reactivity of the anti-PrP antibody described herein against $PrP^{Res}$ of both Scrapie (139A and ME7) and Creutzfeldt-Jakob disease (CJD).

Figure 6:
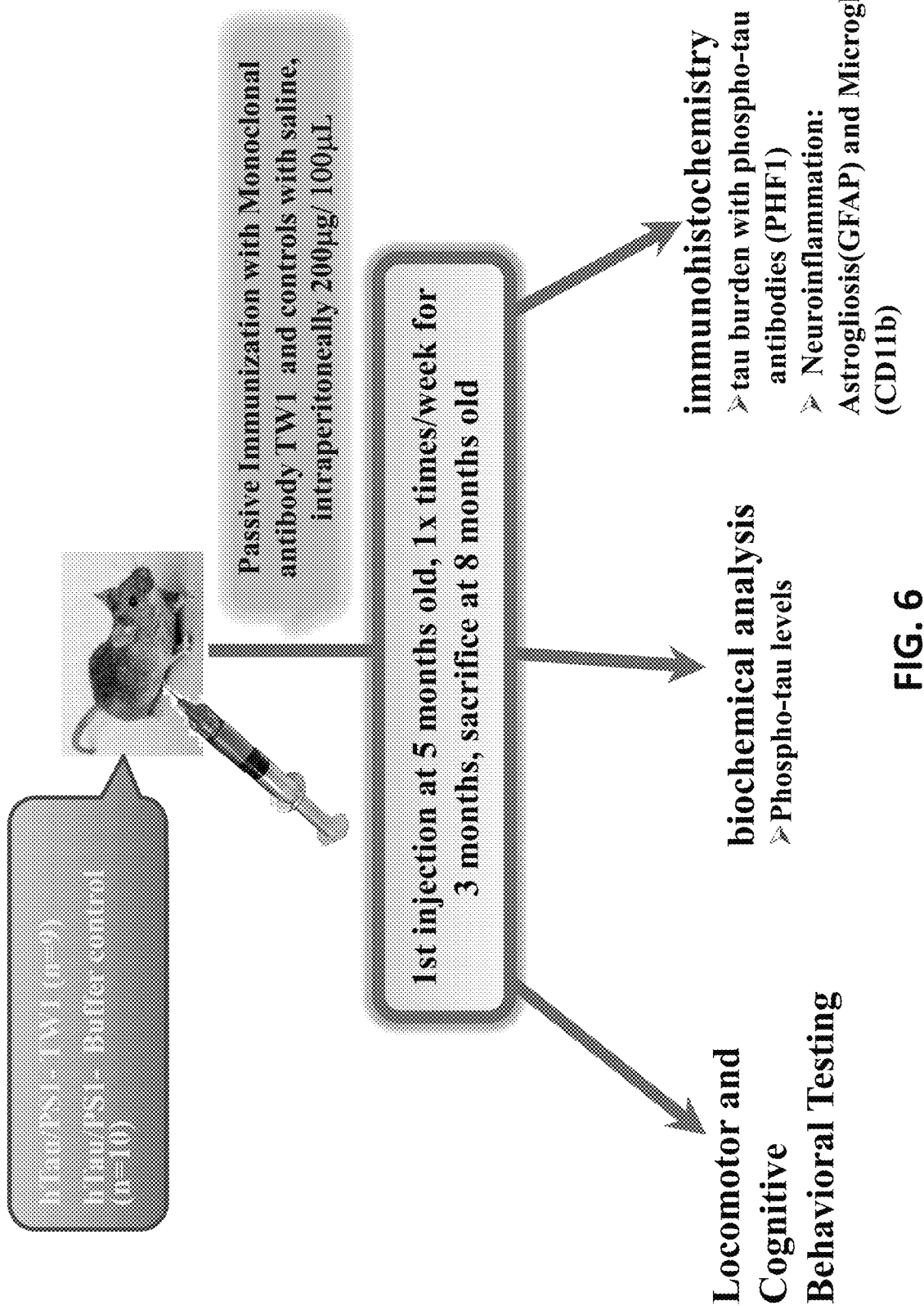

FIG. 6 is a schematic of the passive anti-PrP antibody immunotherapy treatment and testing schedule in the hTau/PS1 transgenic mouse model.

Figure 7:
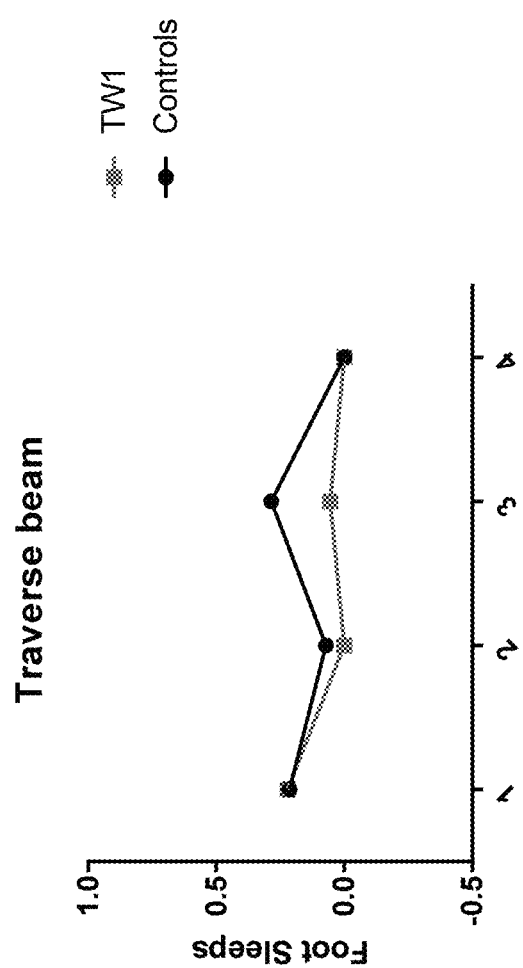

FIG. 7 is a graph tracking traverse beam locomotor activity in hTau/PS1 transgenic mice treated with the anti-PrP antibody described herein (TW1) or vehicle control (controls).

Figure 8:
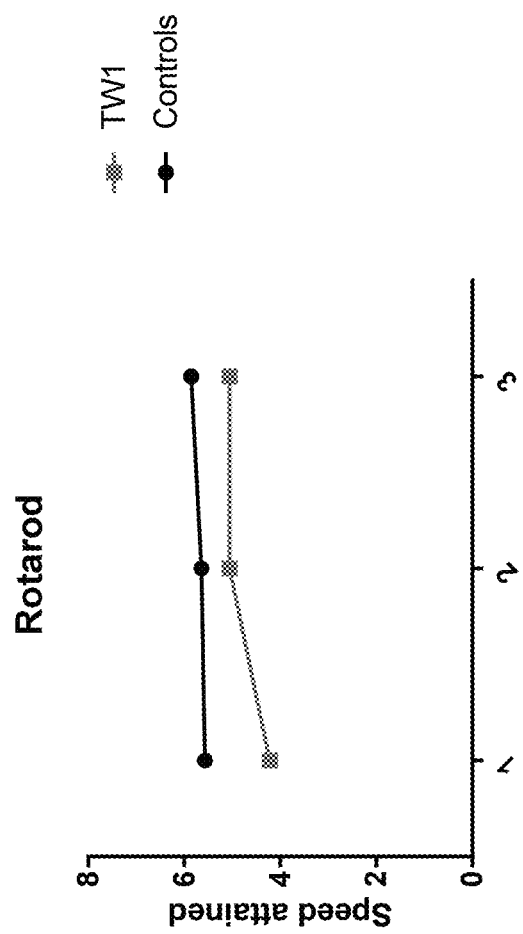

FIG. 8 is a graph showing rotarod locomotor activity in hTau/PS1 transgenic mice treated with the anti-PrP antibody described herein (TW1) or vehicle control (controls).

Figure 9:
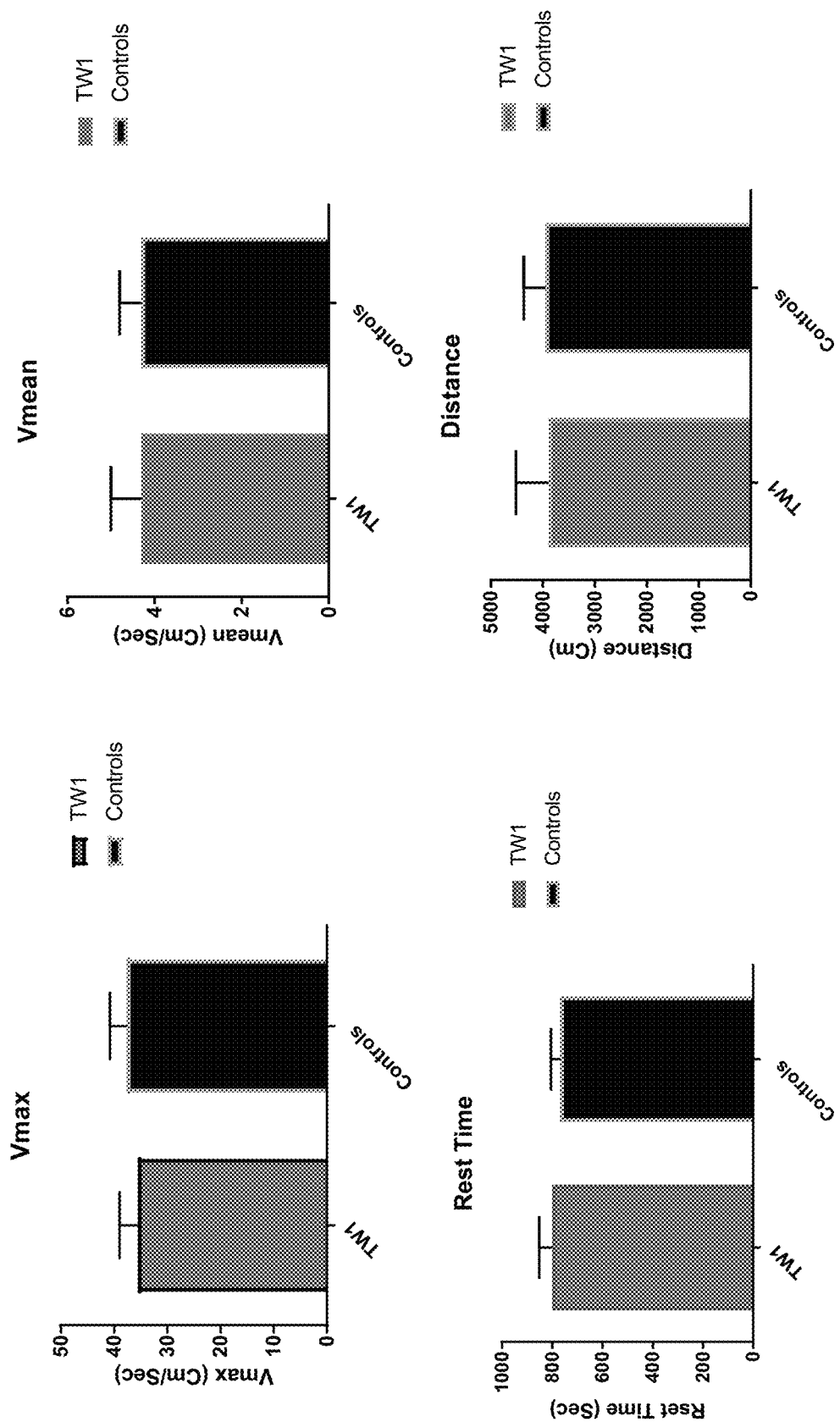

FIG. 9 is a series of graphs showing locomotor activity in hTau/PS1 transgenic mice treated with the anti-PrP antibody described herein (TW1) or vehicle control (controls).

Figure 10:
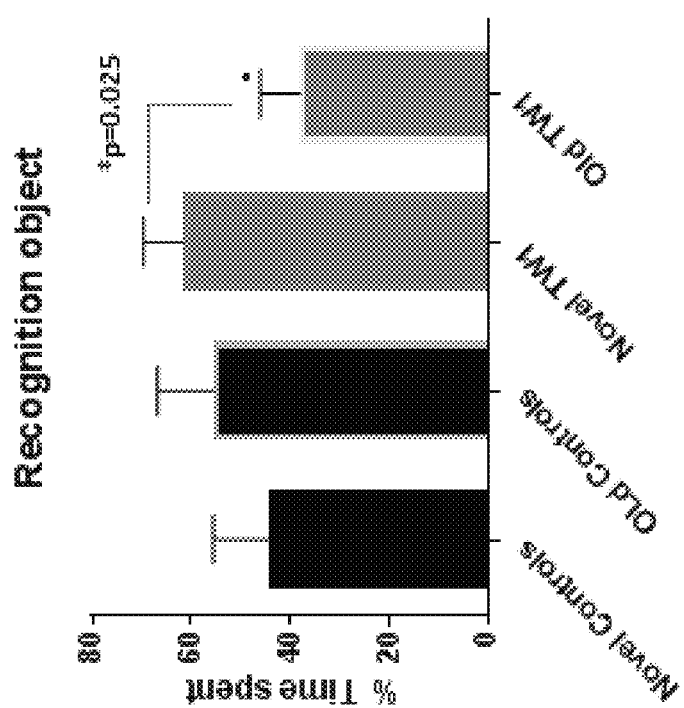

FIG. 10 is a graph showing novel object recognition testing in hTau/PS1 transgenic mice treated with the anti-PrP antibody as described herein (TW1) or vehicle control (controls).

FIGS. 11A-11C are graphs showing the results of closed field symmetrical maze testing in hTau/PS1 transgenic mice treated with the anti-PrP antibody as described herein or vehicle control at days 1 (FIG. 11A), 2 (FIG. 11B), and 3 (FIG. 11C) following treatment.

Figures 12A, 12B, 12C:
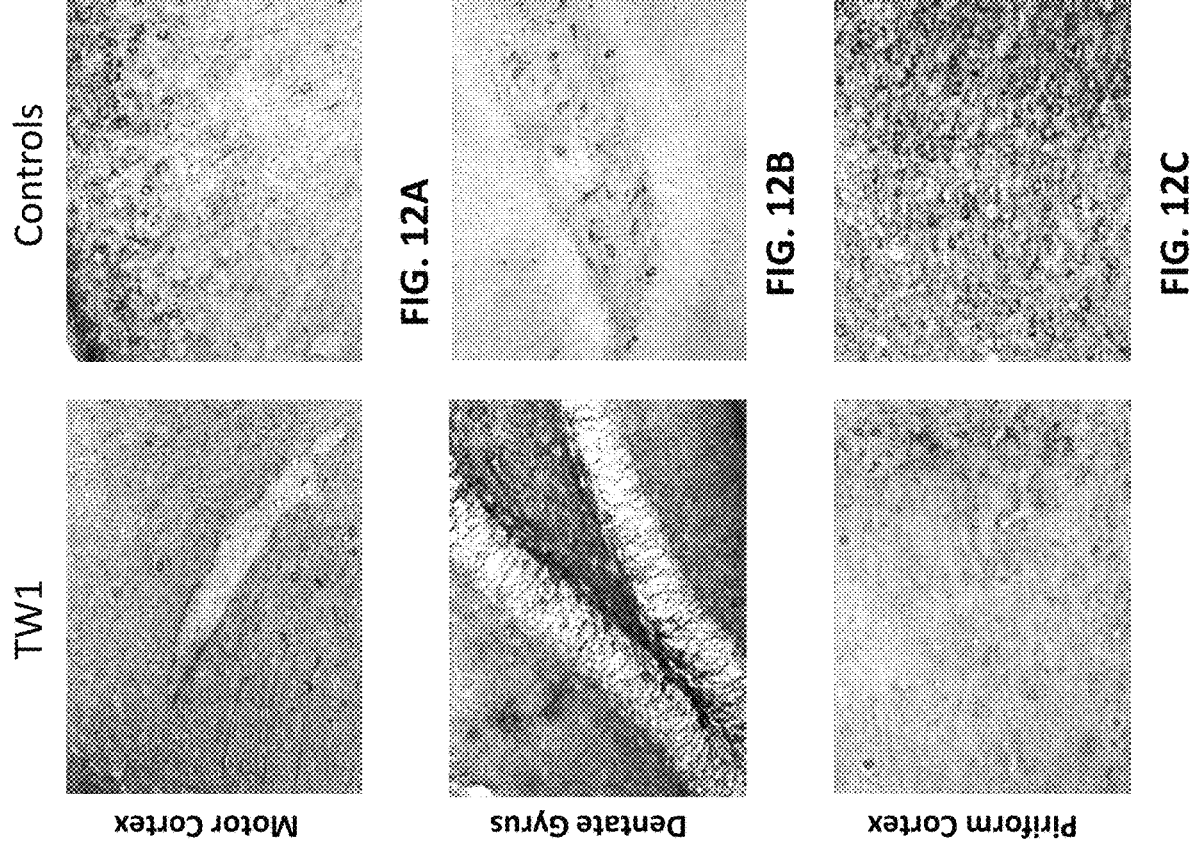

FIGS. 12A-12C shows PHF1 immunoreactivity with tau in the motor cortex (FIG. 12A), dentate gyrus (FIG. 12B), and piriform cortex (FIG. 12C) of hTau/PS1 transgenic mice treated with the anti-PrP antibody described herein (TW1) or vehicle control (controls). The graphs in FIGS. 12A, 12B, and 12C show quantitative assessment of the PHF1 immunolabeling of tau shown in the images on the left.

Figures 13A, 13B:
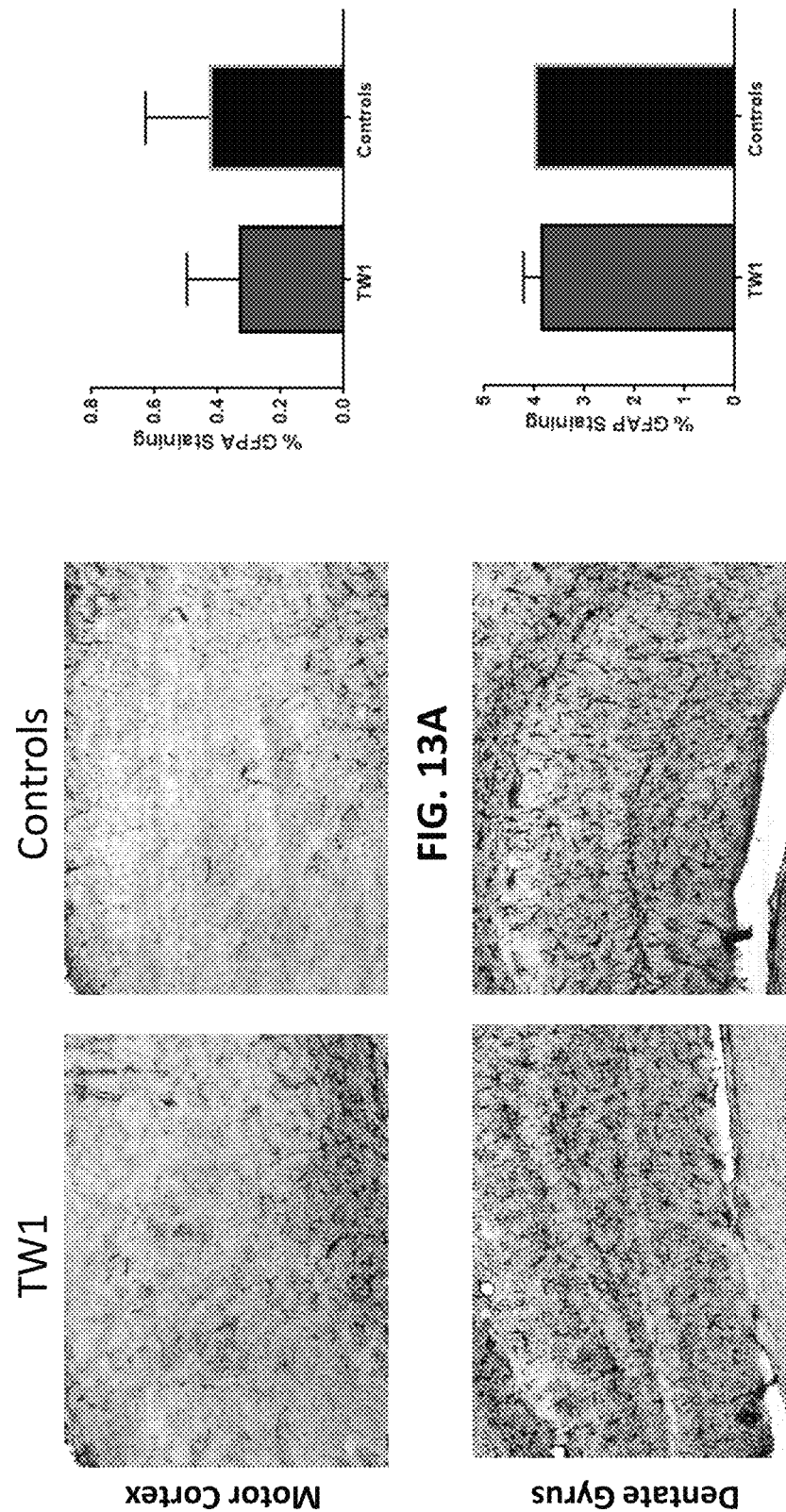

FIGS. 13A-13B show GFAP immunoreactivity in the motor cortex (FIG. 13A) and dentate gyrus (FIG. 13B) of hTau/PS1 transgenic mice treated with the TW1 anti-PrP antibody described herein (left images) or vehicle control (right images). The graphs in FIGS. 13A and 13B show quantitative assessment of the GFAP immunolabeling.

Figure 14A:
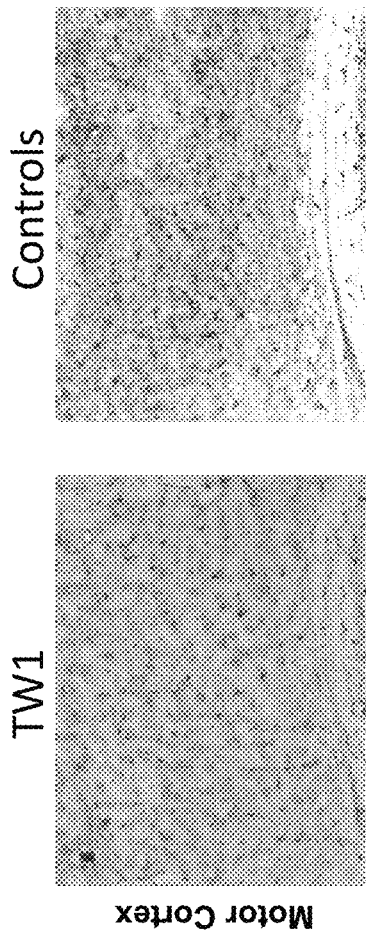
Figure 14B:
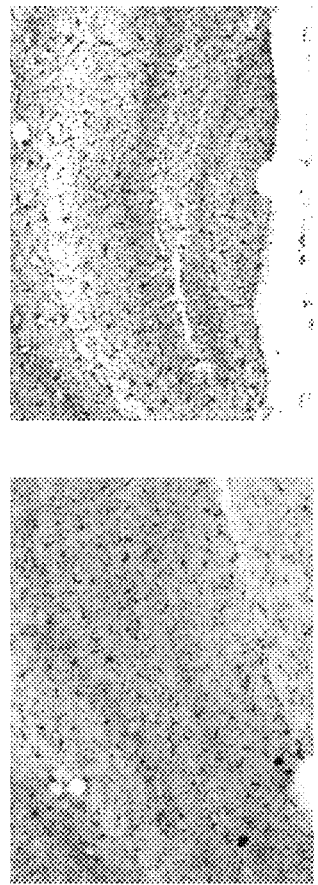

FIGS. 14A-14B show Iba1 immunoreactivity in the motor cortex (FIG. 14A) and dentate gyrus (FIG. 14B) of hTau/PS1 transgenic mice treated with the TW1 anti-PrP antibody described herein (left images) or vehicle control (right images). The graphs in FIGS. 14A and 14B show quantitative assessment of the Iba1 immunolabeling.

FIGS. 15A-15B show biochemical analysis of pathological Tau in brains of hTau/PS1 transgenic mice treated with the anti-PrP antibody of the invention or vehicle control. FIG. 15A are the western blots showing tubulin and soluble Tau (PHF-1) immunoreactivity levels in brain tissue. FIG. 15B are graphs providing a quantitative assessment of tubulin level (left), PHF-1 level (middle), and the PHF1/tubulin ratio (right) in hTau/PS1 transgenic mice treated with the TW1 anti-PrP antibody described herein or vehicle control. TW1 therapy reduced the ratio of pathological soluble tau to tubulin by 40%.

DETAILED DESCRIPTION OF THE INVENTION

A first aspect of the present invention is directed to an antibody or binding fragment thereof that binds prion protein. In particular, the antibody or binding fragment as disclosed herein binds to human prion protein. As described herein the antibody or binding fragment thereof of the present disclosure binds to an epitope within human prion protein involved in mediating the toxicity of proteins or peptides in their toxic oligomeric form, such as amyloid-beta oligomer toxicity, tau oligomer toxicity, and prion protein oligomer toxicity.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired binding activity, i.e., binding to wildtype prion protein ($PrP^c$).

In one embodiment, the antibody of the disclosure is an immunoglobulin (Ig) molecule and comprises four polypeptide chains, i.e., two heavy (H) chains and two light (L) chains linked by disulfide bonds. Five types of mammalian Ig heavy chains are known: α, δ, ε, γ, and μ, wherein the type of heavy chain defines the class (isotype) of the antibody. Antibodies of the disclosure can be of any class (e.g., IgG, IgE, IgM, IgD, and IgA), and subclass (e.g., IgG1, IgG2, IgG3, IgG4, IgA1 and IgA2). The heavy chain may contain two regions, the constant region ($C_H$) and the variable region ($V_H$). The constant region shares high homology in all naturally occurring antibodies of the same isotype within the same species. Like the heavy chain, a light chain may also consist of one constant domain ($C_L$) and one variable domain ($V_L$). In mammals there are two types of immunoglobulin light chain, lambda (λ) and kappa (κ). The unique binding property or antigen binding specificity of a given antibody is determined by the variable (V) regions. In particular, three variable loops in each the light ($V_L$) and the heavy ($V_H$) chains, known as complementarity determining regions (CDR), are responsible for the antigen binding specificity. These regions are described in more detail infra.

An antibody fragment of the disclosure is a molecule containing an antigen binding region or antigen binding domain of a full antibody, e.g., the $V_H$ region, the $V_L$ region, or a combination of both regions. In one embodiment, the antibody fragment comprises a single-chain polypeptide containing one, two, or three of the CDRs of the light-chain variable domain. In another embodiment, the antibody fragment comprises a single-chain polypeptide containing one, two, or three of the CDRs of the heavy chain variable region. In another embodiment, the antibody fragment of the disclosure is a single domain antibody (also referred to as a nanobody), e.g., a peptide chain of about 110 amino acids long comprising one heavy chain variable region domain or one light chain variable region domain of a full antibody. In another embodiment, the antibody fragment is a fragment antigen-binding (F(ab)) fragment or a F(ab')$_2$ fragment.

Antibodies and antibody fragments of the present disclosure also encompass mutants, variants, or derivatives of the disclosed antibodies or fragments thereof which retain the essential epitope binding features of an Ig molecule. For example, the single domain antibodies can be derived from camelid ($V_H$H domains) or cartilaginous fish (V-NAR) variable domains, alone or fused to an Fc domain. In another embodiment, the antibody fragment comprises the heavy chain and light chain variable regions fused together to form a single-chain variable domain antibody (scFv) or a single-chain variable domain with an Fc portion (i.e., a scFv-Fc, e.g., a minibody). In another embodiment, the antibody fragment is a divalent or bivalent single-chain variable fragment, engineered by linking two scFvs together either in tandem (i.e., tandem scFv), or such that they dimerize to form diabodies. In yet another embodiment, the antibody is a trivalent single chain variable fragment, engineered by linking three scFvs together, either in tandem or in a trimer formation to form triabodies. In another embodiment, the antibody is a tetrabody single chain variable fragment. In another embodiment, the antibody is a "linear antibody" which is an antibody comprising a pair of tandem Fd segments ($V_H$—$C_H$1-$V_H$—$C_H$1) that form a pair of antigen binding regions (see Zapata et al. *Protein Eng.* 8(10):1057-1062 (1995), which is hereby incorporated by reference in its entirety).

Antibody and antibody fragments disclosed herein can be mono-valent, bi-valent, or tri-valent with regard to binding domains, and the binding domains may be mono-specific, bi-specific, or tri-specific in binding specificity by design.

As noted above, the $V_H$ and $V_L$ regions of an antibody are subdivided into regions of hypervariability, termed complementarity determining regions (CDR). The CDRs are interspersed with regions that are more conserved in each family of V genes, termed framework regions (FR). These FR regions are specific to place in the proper spatial configuration so as to contact amino acid residues of the CDRs that are responsible for most of the binding capacity of the antibody. Each $V_H$ and $V_L$ is composed of three CDRs and four FRs, arranged from amino-terminus to carboxy-terminus in the following order: FR1, CDR1, FR2, CDR2, FR3, CDR3, FR4.

The three CDRs in each of the variable regions of the heavy chain and the light chain are designated CDR1, CDR2 and CDR3 for each of the variable regions (i.e., (L-CDR1, 2 and 3 of light chain and H-CDR1, 2, and 3 of heavy chain). The term "CDR set" refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991), which is hereby incorporated by reference in its entirety) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, *J. Mol. Biol.* 196:901-917 (1987) and Chothia et al., *Nature* 342:877-883 (1989) which are hereby incorporated by reference in their entirety, describe certain sub-portions within Kabat CDRs that adopt nearly identical peptide backbone conformations, despite having great diversity at the level of amino acid sequence. These regions may be referred to as Chothia CDRs, which have boundaries that overlap with Kabat CDRs. Other boundaries defining CDRs overlapping with the Kabat CDRs have been described by Padlan, *FASEB J.* 9:133-139 (1995) and MacCallum, *J Mol Biol* 262(5):732-45 (1996), which are hereby incorporated by reference in their entirety.

In one embodiment, the CDRs and FRs of the heavy and light chain variable regions of the antibody or fragment thereof of the present disclosure are defined in accordance with KABAT et al., "Sequences of Proteins of Immunological interest" 5$^{th}$ ed. (1991), which is hereby incorporated by reference in its entirety. In accordance with the Kabat system, an antibody of the present disclosure comprises a heavy chain variable region where FR1 encompasses residues 1-30 (after the leader sequences) and contains a conserved cysteine (Cys) residue at position 22. CDR1 region extends from residue 31 to about residue 35. The residue at position 35 is defined by the conserved tryptophan (Trp) residue at position 36, which is essential for antibody folding. The CDR1 may contain up to 2 residue insertions (i.e., 35A and 35B). FR2 of the heavy chain variable region begins at the tryptophan residue at about position 36 and extends up to a duplet Isoleucine-Glycine (Ile-Gly) at position 48-49 in some $V_H$ families or Leucine (Leu) at position 48 and Alanine (Ala), Serine (Ser) at position 49 in other $V_H$ families. CDR2 of the $V_H$ extends from residue 50 to residue 65 with 3 possible insertions in the middle of the CDR (typically 17-20 residues in length). The third framework of the $V_H$ extends from the conserved Arginine (Arg) or Lysine (Lys) residue at position 66 to position 94, which is two amino acid residues after the consensus Cys residue at position 92. FDR3 may comprise 3 insertions, therefore ranging between 29-32 amino acid residues in total. CDR3 starts at residue 95, as defined by the conserved Cys at position 92, is between 3-25 amino acid residues in length, and is made by the recombination of three different genes, i.e. a VH gene of any family, a partial or complete DH gene, and a JH gene.

In accordance with the Kabat numbering system, the FR1 of the light chain variable region ($V_L$) of an antibody or fragment thereof as described herein extends from residue 1 (after the leader sequence) to the conserved Cys at residue 23. CDR1 begins after the conserved Cys residue, i.e., at position 24 and extends 10-17 residues to the amino acid residue before the conserved Trp residue at about position 35. The Trp residue is essential for antibody folding. The second framework of the $V_L$ begins at the conserved Trp residue and extends to the conserved Tyrosine (Tyr) at position 49. CDR2 of the $V_L$ extends from position 50 after the conserved Tyr residue to position 56, ending before the conserved Gly residue or equivalent at position 57. CDR2 typically has seven amino acid residues or less. The third framework begins at the consensus Gly at position 57 and extends to the Cys as position 88. The cysteine at position 88 forms the disulfide bridge with the conserved cysteine at position 23. CDR3 of the $V_L$ starts at position 89 (after the consensus Cys at position 88) and extends to position 97. Residues 97 and 98 are conserved threonine and phenylalanine. The length of CDR3 is made by the recombination of two different genes, i.e. a VL gene of any family and a JL gene. Thus, the length of CDR3 varies as it may contain up to six amino acid residue insertions. The fourth framework region begins at position 98 and extends through position 107.

In one embodiment, the antibody or binding fragment thereof described herein is a chimeric antibody. A chimeric antibody is an antibody where one portion of the amino acid sequence of each of the heavy and light chains is homologous to corresponding sequences in an antibody derived from a particular species or belonging to a particular class, while the remaining segment of each chain is homologous to corresponding sequences in another species or class. Typically the variable region of both light and heavy chains mimics the variable regions of antibodies derived from one species of mammals, while the constant portions are homologous to sequences of antibodies derived from another mammalian species. For example, the variable region can be derived from presently known sources using readily available B-cells or hybridomas from non-human host organisms in combination with constant regions derived from, for example, human cell preparations. Methods of making chimeric antibodies are well known in the art, see e.g., U.S. Pat. No. 4,816,567; and Morrison et al., "Chimeric human antibody molecules: mouse antigen-binding domains with human constant region domains" *Proc. Natl. Acad. Sci. USA* 81:6851-6855 (1984), which are hereby incorporated by reference in their entirety).

In another embodiment, the antibody or binding fragment thereof is a CDR-grafted antibody. A "CDR-grafted antibody" is an antibody which comprises heavy and light chain variable region sequences of one species, where one or more of the CDR regions are replaced with CDR regions of another species. For example, in one embodiment the CDR grafted antibody comprises human or humanized heavy and light chain variable regions, where one or more of the CDRs within these regions is replaced with one or more CDRs from another species, e.g., murine CDRs.

In another embodiment, the antibody or binding fragment thereof is a humanized antibody. A humanized antibody is an antibody or a variant, derivative, analog or portion thereof which comprises a framework region having substantially the amino acid sequence of a human antibody and a complementary determining region having substantially the amino acid sequence of a non-human antibody. As used herein, the term "substantially" in the context of a CDR refers to a CDR having an amino acid sequence that is at least 65%, at least 70%, at least 75%, at least 80%, at least 85%, at least 90%, at least 95%, at least 98% or at least 99% identical to the amino acid sequence of a non-human antibody CDR. Likewise, the term "substantially" in the context of a FR refers to a FR having an amino acid sequence that is at least 65%, at least 70%, at least 75%, at least 80%, at least 85%, at least 90%, at least 95%, at least 98% or at least 99% identical to the amino acid sequence of a human FR. A humanized antibody comprises substantially all of at least one, and typically two, variable domains (Fab, Fab', F(ab')$_2$, Fv) in which all or substantially all of the CDR regions correspond to those of a non-human immunoglobulin (i.e., the donor antibody) and all or substantially all of the framework regions are those of a human or humanized immunoglobulin framework sequence (i.e., the acceptor antibody).

Methods of humanizing antibodies are well known in the art, see e.g., Almagro and Fransson, "Humanization of Antibodies," *Frontiers in Bioscience* 13:1619-1633 (2008), U.S. Pat. No. 6,054,297 to Carter et al., U.S. Pat. No. 8,343,489, and U.S. Patent Application Publication No. US20100261620 to Almagro et al., which are hereby incorporated by reference in their entirety. The human or humanized framework sequences can be chosen based on known structure, i.e., a fixed framework sequence, sequence homology to the framework sequences of the donor antibody (e.g., the antibody from which the CDRs are derived), i.e., a best-fit framework sequence, or a combination of both approaches. Regardless of the method chosen to select the human framework sequence, the sequences can be selected from mature framework sequences, germline gene sequences, or consensus framework sequences. Compatible human framework sequences are those that are similar in both length and sequence to the framework sequence of the donor antibody sequence (i.e., the antibody from which the CDRs are derived) to ensure proper folding of the antibody and binding domain formation.

In one embodiment, the humanized framework sequence of a humanized antibody of the disclosure comprises a consensus framework sequence. A consensus framework sequence is derived from a consensus immunoglobulin sequence, which is the sequence formed from the most frequently occurring amino acids (or nucleotides) in a family of related immunoglobulin sequences (see e.g., WINNAKER, "From Genes to Clones: Introduction to Gene Technology" (1987); Carter et al., *Proc. Natl. Acad. Sci. USA*, 89:4285 (1992); and Presta et al., *J. Immunol.*, 151:2623 (1993), which are hereby incorporated by reference in their entirety). In a family of immunoglobulins, each position in the consensus sequence is occupied by the amino acid residue occurring most frequently at that position in the family. If two amino acids occur equally frequently, either can be included in the consensus sequence.

In another embodiment, a humanized antibody or binding fragment thereof as disclosed herein comprises a fixed framework region. Human heavy chain and light chain FR sequences known in the art can be used as heavy chain and light chain "acceptor" framework sequences (or simply, "acceptor" sequences) to humanize a non-human antibody using techniques known in the art (see e.g., Sims et al., *J. Immunol.*, 151:2296 (1993); Chothia et al., *J. Mol. Biol.*, 196:901 (1987), which are hereby incorporated by reference in their entirety). In one embodiment, human heavy chain and light chain acceptor sequences are selected from the framework sequences listed in publically available databases such as V-base or in the international ImMunoGeneTics® (IMGT®) information system.

Humanized antibodies or binding fragments thereof as described herein may also comprise at least a portion of an immunoglobulin constant region (Fc), typically that of a human immunoglobulin. In one embodiment, the humanized antibody disclosed herein comprises the light chain as well as at least the variable domain of a heavy chain. The humanized antibody may further comprise the CH1, hinge, CH2, CH3, and CH4 regions of the heavy chain. In another embodiment, the humanized antibody comprises only a humanized light chain. In another embodiment, the humanized antibody comprises only a humanized heavy chain. In another embodiment, the humanized antibody comprises only a humanized variable domain of a light chain and/or a humanized variable domain of a heavy chain.

Humanized antibodies and binding fragments thereof as described herein may be selected from any class of immunoglobulins, including IgM, IgG, IgD, IgA and IgE, and any isotype, including without limitation IgG1, IgG2, IgG3 and IgG4. The humanized antibody or binding fragment thereof may comprise sequences from more than one class or isotype, and particular constant domains may be selected to optimize desired effector functions using techniques well-known in the art.

In one embodiment, the antibodies and binding fragments thereof as described herein are human antibodies. Method of producing human antibodies that are known in the art are suitable for use in accordance with the present disclosure. For example, one can produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl Acad. Sci. USA* 90:2551 (1993); Jakobovits et al., *Nature*

362:255-258 (1993); U.S. Pat. No. 5,545,806 to Lonberg et al, U.S. Pat. No. 5,569,825 to Lonberg et al, and U.S. Pat. No. 5,545,807 to Surani et al, which are hereby incorporated by reference in their entirety.

Alternatively, phage display technology (McCafferty et al., *Nature* 348:552-553 (1990), which is hereby incorporated by reference in its entirety) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, see e.g., Johnson and Chiswell, *Current Opinion in Structural Biology* 3:564-571 (1993), which is hereby incorporated by reference in its entirety. Several sources of V-gene segments can be used for phage display (see e.g., Clackson et al., *Nature* 352:624-628 (1991), which is hereby incorporated by reference in its entirety). A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), Griffith et al., *EMBO J* 12:725-734 (1993), see e.g., U.S. Pat. No. 5,565,332 to Hoogenboom and U.S. Pat. No. 5,573,905 to Lerner et al., which are hereby incorporated by reference in their entirety.

The antibodies and binding fragments thereof described herein can be human antibodies or humanized antibodies (fully or partially humanized) as described supra. Alternatively, the antibodies and binding fragments thereof can be animal antibodies such as, but not limited to, a bird (for example, a duck or a goose), a shark, a whale, or a mammal, including a non-primate (for example, a cow, pig, camel, llama, horse, goat, rabbit, sheep, hamster, guinea pig, cat, dog, rat, mouse, etc.) or a non-human primate (for example, a monkey, a chimpanzee, etc.).

Methods of antibody production, in particular, monoclonal antibody production, may be carried out using the methods described herein and those well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of an animal which has been previously immunized with the antigen of interest (e.g., a non-denatured PK-resistant fragment of $PrP^C$ or the scrapie form of the prion protein ($PrP^{Sc}$) as described in the Examples herein) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

In another embodiment, monoclonal antibodies can be isolated from antibody phage libraries generated using the techniques described in McCafferty et al., "Phage Antibodies: Filamentous Phage Displaying Antibody Variable Domains," *Nature* 348:552-554 (1990), which is hereby incorporated by reference in its entirety. Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety, describe the isolation of murine and human antibodies, respectively, using phage libraries. Subsequent publications describe the production of high affinity (nM range) human antibodies by chain shuffling (Marks et al., *BioTechnology* 10:779-783 (1992), which is hereby incorporated by reference in its entirety), as well as combinatorial infection and in vivo recombination as a strategy for constructing very large phage libraries (Waterhouse et al., *Nuc. Acids. Res.* 21:2265-2266 (1993), which is hereby incorporated by reference in its entirety). Thus, these techniques are viable alternatives to traditional monoclonal antibody hybridoma techniques for isolation of monoclonal antibodies.

Alternatively, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, generate monoclonal antibodies.

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

In one embodiment, the anti-PrP antibody or binding fragment thereof as described herein comprises a heavy chain variable region. The heavy chain variable region comprises a complementarity-determining region 1 (H-CDR1) comprising an amino acid sequence of SEQ ID NO: 1 (EDYYIH), or a modified amino acid sequence of SEQ ID NO: 1, said modified sequence containing 1 or 2 amino acid residue modifications as compared to SEQ ID NO: 1. The heavy chain variable region further comprises a complementarity-determining region 2 (H-CDR2) comprising an amino acid sequence of SEQ ID NO: 2 (WIGRID-PEDDETKYAPKF), or a modified amino acid sequence of SEQ ID NO: 2, said modified sequence containing 1, 2, 3, or 4 amino acid residue modifications as compared to SEQ ID NO: 2. The heavy chain variable region further comprises a complementarity-determining region 3 (H-CDR3) comprising an amino acid sequence of SEQ ID NO: 3 (RFD-GIGDYSDS), or a modified amino acid sequence of SEQ ID NO: 3, said modified sequence containing 1, 2, or 3 amino acid residue modifications as compared to SEQ ID NO: 3.

The antibody or binding fragment thereof as described herein may further comprise a light chain variable region. The light chain variable region comprises a complementarity-determining region 1 (L-CDR1) having an amino acid sequence of SEQ ID NO: 5 (SLLASDEQ), or a modified amino acid sequence of SEQ ID NO: 5, said modified sequence containing 1 or 2 amino acid residue modifications as compared to SEQ ID NO: 5. The light chain variable region further comprises a complementarity-determining region 2 (L-CDR2) having an amino acid sequence of SEQ ID NO: 6 (LMYLGSK LDS), or a modified amino acid sequence of SEQ ID NO: 6, said modified sequence containing 1 or 2 amino acid residue modifications as compared to SEQ ID NO: 6. The light chain variable region further comprises a complementarity-determining region 3 (L-CDR3) having an amino acid sequence of SEQ ID NO: 7 (WQGTHFPQT), or a modified amino acid sequence of SEQ ID NO: 7, said modified sequence containing 1 or 2 amino acid residue modifications as compared to SEQ ID NO: 7.

Suitable amino acid modifications to the heavy chain CDR sequences and/or the light chain CDR sequences of the anti-PrP antibody disclosed herein include, for example, conservative substitutions or functionally equivalent amino acid residue substitutions that result in variant CDR sequences having similar or enhanced binding characteristics to those of the CDR sequences disclosed herein. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981, which is hereby incorporated by reference in its entirety). Non-conservative substitutions can also be made to the heavy chain CDR sequences and the light chain CDR sequences as disclosed herein. Non-conservative substitutions involve substituting one or more amino acid residues of the CDR with one or more amino acid residues from a different class of amino acids to improve or enhance the binding properties of CDR.

The amino acid sequences of the heavy chain variable region CDRs of and/or the light chain variable region CDRs of the anti-PrP antibody described herein may further comprise one or more internal neutral amino acid insertions or deletions that do not alter prion protein binding. In one embodiment, the H-CDR3 having an amino acid sequence of SEQ ID NO: 3, further contains one or more internal neutral amino acid insertions or deletions that do not alter prion protein binding. In another embodiment, the L-CDR1, having an amino acid sequence of SEQ ID NO: 5 further contains one or more internal neutral amino acid insertions or deletions that do not alter prion protein binding.

In one embodiment of the present disclosure, the anti-PrP antibody or binding fragment thereof comprises a heavy chain variable region with a H-CDR1 having the amino acid sequence of SEQ ID NO: 1; a H-CDR2 having the amino acid sequence of SEQ ID NO: 2; and a H-CDR3 having the amino acid sequence of SEQ ID NO: 3. An exemplary heavy chain variable region comprising the aforementioned CDR regions has the amino acid sequence of SEQ ID NO: 4 as shown below. The CDR regions of the variable heavy chain of SEQ ID NO: 4 are underlined and the flanking framework regions (i.e., FR1-FR4) are shown in bold.

```
                                              (SEQ ID NO: 4)
M Q E S G A E L V K P G A S V K L S C T V A G F N

I E D Y Y I H W V K Q R P E Q G L E W I G R I D P

E D D E T K Y A P K F L G K A T V T S D T S S N T

V F L Q L R S L T S E D T A I Y Y C G R F D G I G

D Y S D S W G Q
```

In one embodiment of the present disclosure, the anti-PrP antibody or binding fragment thereof comprises a light chain variable region with a L-CDR1 having the amino acid sequence of SEQ ID NO: 5; a L-CDR2 having the amino acid sequence of SEQ ID NO: 6; and a L-CDR3 having the amino acid sequence of SEQ ID NO: 7. An exemplary light chain variable region comprising the aforementioned CDR regions has the amino acid sequence of SEQ ID NO: 8 as shown below. The CDR regions of the variable light chain of SEQ ID NO: 8 are underlined and the framework regions (i.e., FR1-FR4) are shown in bold.

```
                                              (SEQ ID NO: 8)
A H S V S I S C K S S Q S L L A S D E Q T Y L N W

L L Q R P G Q S P K R L M Y L G S K L D S G V P D

R F T G C G S G T D F T L K I S R V E A E D L G V

Y Y C W Q G T H F P Q T F G G G T K L E I K R
```

In one embodiment, the anti-PrP antibody or binding fragment thereof as described herein comprises a heavy chain variable region having an amino acid sequence of SEQ ID NO: 4 and/or a light chain variable region having an amino acid sequence of SEQ ID NO:8.

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 4, and/or a light chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 8.

In one embodiment, the antibody or binding fragment thereof of the present disclosure comprises a humanized variant of the heavy chain variable region of SEQ ID NO: 4 and/or a humanized variant of the light chain variable region of SEQ ID NO: 8, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NOs: 4 and 8), or a combination of these approaches. The humanized framework regions are designed to be similar in length and sequence to the parental framework sequences of SEQ ID NO: 4 and SEQ ID NO: 8, respectively. In one embodiment, the humanized framework regions share 50%, 55%, 60%, 65%, 70%, 75%, 80%, 85%, 90%, 95% or more sequence identity to the framework regions of SEQ ID NO:4 and SEQ ID NO: 8, respectively. In another embodiment, the humanized framework regions are 60%, 65%, 70%, 75%, 80%, 85%, 90%, 95% or more similar in length to the framework regions of SEQ ID NO:4 and SEQ ID NO: 8, respectively. Humanized variants of the heavy chain variable region of SEQ ID NO: 4 and the light chain variable region of SEQ ID NO: 8 share at least 50%, at least 55%, at least 60%, at least 65%, at least 70%, at least 75%, at least 80%, at least 85%, at least 90%, at least 95% sequence identity along the entire length of SEQ ID NO: 4 and SEQ ID NO: 8, respectively.

Antibody "specificity" refers to selective recognition of the antibody or binding portion thereof as described herein for a particular epitope of prion protein. The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. The epitope of the antibodies described herein may be "linear" or "conformational". In a linear epitope, all of the points of interaction between the protein and the antibody occur linearly along the primary amino acid sequence of the protein. In a conformational epitope, the points of interaction occur across amino acid residues on the protein that are separated from one another, i.e., noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, 6, 7, 8, 9, 10, 11, 12, 13, 14, 15, 16, 17, 18, 19, 20 or more amino acids in a unique spatial conformation. Antibodies that recognize the same epitope can be verified in a simple immunoassay showing the ability of one antibody to block the binding of another antibody to a target antigen.

The antibody or binding fragment thereof as described herein binds to prion protein. In particular, the antibody or binding fragment thereof binds to an epitope of prion protein that includes or comprises the region of prion that interacts with toxic oligomeric proteins or peptides, such as, e.g., toxic amyloid-β oligomers, toxic tau oligomers, and toxic prion protein oligomers. Binding of the antibodies described herein to this epitope of prion inhibits the interaction between prion and these toxic oligomeric proteins or peptides. This epitope is located within and corresponds to amino acid residues 94-108 of human prion protein (UniProt Accession No. P04156-1) having the amino acid sequence of SEQ ID NO: 9 as shown below.

```
Met Ala Asn Leu Gly Cys Trp Met Leu Val Leu Phe
1               5                   10
Val Ala Thr Trp Ser Asp Leu Gly Leu Cys Lys Lys
        15                  20
Arg Pro Lys Pro Gly Gly Trp Asn Thr Gly Gly Ser
25                  30                  35
Arg Tyr Pro Gly Gln Gly Ser Pro Gly Gly Asn Arg
            40                  45
Tyr Pro Pro Gln Gly Gly Gly Trp Gly Gln Pro
    50                  55                  60
His Gly Gly Gly Trp Gly Gln Pro His Gly Gly Gly
                65                  70
Trp Gly Gln Pro His Gly Gly Gly Trp Gly Gln Pro
        75                  80
His Gly Gly Gly Trp Gly Gln Gly Gly Gly Thr His
85                  90                  95
Ser Gln Trp Asn Lys Pro Ser Lys Pro Lys Thr Asn
            100                 105
Met Lys His Met Ala Gly Ala Ala Ala Ala Gly Ala
    110                 115                 120
Val Val Gly Gly Leu Gly Gly Tyr Met Leu Gly Ser
                125                 130
Ala Met Ser Arg Pro Ile Ile His Phe Gly Ser Asp
        135                 140
Tyr Glu Asp Arg Tyr Tyr Arg Glu Asn Met His Arg
145                 150                 155
Tyr Pro Asn Gln Val Tyr Tyr Arg Pro Met Asp Glu
            160                 165
Tyr Ser Asn Gln Asn Asn Phe Val His Asp Cys Val
    170                 175                 180
Asn Ile Thr Ile Lys Gln His Thr Val Thr Thr Thr
                185                 190
Thr Lys Gly Glu Asn Phe Thr Glu Thr Asp Val Lys
        195                 200
Met Met Glu Arg Val Val Glu Gln Met Cys Ile Thr
205                 210                 215
Gln Tyr Glu Arg Glu Ser Gln Ala Tyr Tyr Gln Arg
            220                 225
Gly Ser Ser Met Val Leu Phe Ser Ser Pro Pro Val
    230                 235                 240
Ile Leu Leu Ile Ser Phe Leu Ile Phe Leu Ile Val
                245                 250
Gly
```

Another aspect of the present disclosure relates to an antibody or binding portion thereof (e.g., a human antibody) that competes for binding to human prion protein with the anti-PrP antibody described herein, i.e., an antibody comprising a heavy chain variable region comprising an H-CDR1 of SEQ ID NO: 1, an H-CDR2 of SEQ ID NO: 2, and an H-CDR3 of SEQ ID NO: 3, and a light chain variable region comprising L-CDR1 of SEQ ID NO: 5, L-CDR2 of SEQ ID NO: 6, and L-CDR3 of SEQ ID NO: 7. In accordance with this aspect of the disclosure, the antibody or binding portion there of competes for binding to human prion protein at an epitope within or comprising amino acid residues 94-108 of human prion protein (SEQ ID NO: 9).

In accordance with this aspect of the disclosure, a competitive binding assay, such as Bio-Layer Interferometry (BLI) can be utilized to identify an antibody or binding portion thereof that competes for binding to a prion protein with the enumerated monoclonal antibody. Other competitive binding assays known in the art can also be utilized to identify a competitive binding antibody in accordance with this aspect of the disclosure.

Another aspect of the present disclosure is directed to an antibody mimetic that binds prion protein. An "antibody mimetic" as referred to herein encompasses any organic compound, e.g., a peptide or polypeptide, that can specifically bind an antigen like an antibody, and is about 3-20 kDa. In one embodiment, the antibody mimetic comprises a scaffold which binds its antigen via amino acids in exposed loops similar to the CDR loops of an antibody. These antibody mimetics include, without limitation, adnectins, lipocalins, Kunitz domain-based binders, avimers, knottins, fynomers, atrimers, and cytotoxic T-lymphocyte associated protein-4 (CTLA4)-based binders (reviewed in Weidle et al., "The Emerging Role of New Protein Scaffold-based Agents for the Treatment of Cancer," *Cancer Genomics & Proteomics* 10:155-168 (2013), which is hereby incorporated by reference in its entirety). In accordance with this aspect of the present disclosure, the loop binding regions of the antibody mimetic are adapted to comprise one or more of the heavy chain and/or light chain CDRs of the antibodies disclosed herein. For example, an antibody mimetic of the present disclosure may comprise a first loop region having an amino acid sequence of SEQ ID NO: 1 or a modified amino acid sequence of SEQ ID NO: 1 said modified sequence containing 1 or 2 amino acid residue modifications as compared to SEQ ID NO: 1. The antibody mimetic may comprise another loop region having an amino acid sequence of SEQ ID NO: 2, or a modified amino acid sequence of SEQ ID NO: 2, said modified sequences containing 1, 2, 3, or 4, amino acid residue modifications as compared to SEQ ID NO: 2. The antibody mimetic may comprise another loop region having an amino acid sequence of SEQ ID NO: 3, or a modified amino acid sequence of SEQ ID NO: 3, said modified sequence containing 1, 2, or 3 amino acid residue modifications as compared to SEQ ID NO: 3. The antibody mimetic may further comprise another loop region having an amino acid sequence of SEQ ID NO: 5, or a modified amino acid sequence of SEQ ID NO: 5, said modified sequence containing 1 or 2 amino acid residue modifications as compared to SEQ ID NO: 5. The antibody mimetic may comprise another loop region having an amino acid sequence of SEQ ID NO: 6, or a modified amino acid sequence of SEQ ID NO: 6, said modified sequence containing 1 or 2 amino acid residue modifications as compared to SEQ ID NO: 6. The antibody mimetic may comprise another loop region having an amino acid sequence of SEQ ID NO: 7, or a modified amino acid sequence of SEQ ID NO: 7, said modified sequence containing 1 or 2 amino acid residue modifications as compared to SEQ ID NO: 7.

In one embodiment, the antibody mimetic comprises one or more modified fibronectin type III (FN3) domains (e.g., an adnectin or centyrin molecule), where each modified FN3 domain has one or more loop regions that comprise one or more CDR sequences or modified CDR sequences as disclosed herein.

The FN3 domain is an evolutionary conserved protein domain that is about 100 amino acids in length and possesses a beta sandwich structure. The beta sandwich structure of human FN3 comprises seven beta-strands, referred to as strands A, B, C, D, E, F, G, with six connecting loops, referred to as loops AB, BC, CD, DE, EF, and FG that exhibit structural homology to immunoglobulin binding domains. Three of the six loops, i.e., loops DE, BC, and FG, correspond topologically to the complementarity determining regions of an antibody, i.e., CDR1, CDR2, and CDR3. The remaining three loops are surface exposed in a manner similar to antibody CDR3. In accordance with the present disclosure, one or more of the loop regions of each FN3 domain of the binding molecule are modified to comprise one or more CDR sequences disclosed herein.

The modified FN3 domain can be a FN3 domain derived from any of the wide variety of animal, yeast, plant, and bacterial extracellular proteins containing these domains. In one embodiment, the FN3 domain is derived from a mammalian FN3 domain. Exemplary FN3 domains include, for example and without limitation, any one of the 15 different FN3 domains present in human tenascin C, or the 15 different FN3 domains present in human fibronectin (FN) (e.g., the $10^{th}$ fibronectin type III domain). Exemplary FN3 domains also include non-natural synthetic FN3 domains, such as those described in U.S. Pat. Publ. No. 2010/0216708 to Jacobs et al., which is hereby incorporated by reference in its entirety. Individual FN3 domains are referred to by domain number and protein name, e.g., the $3^{rd}$ FN3 domain of tenascin (TN3), or the $10^{th}$ FN3 domain of fibronectin (FN10).

Another aspect of the present disclosure is directed to isolated polynucleotides encoding the antibody or binding fragment thereof or antibody mimetic as described herein. In one embodiment, the isolated polynucleotide encodes the heavy chain variable region having the amino acid sequence of SEQ ID NO: 4. In another embodiment, the isolated polynucleotide encodes the light chain variable region having the amino acid sequence of SEQ ID NO: 8. The nucleic acid molecules described herein include isolated polynucleotides, portions of expression vectors or portions of linear DNA sequences, including linear DNA sequences used for in vitro transcription/translation, and vectors compatible with prokaryotic, eukaryotic or filamentous phage expression, secretion, and/or display of the antibodies or binding fragments thereof described herein.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the disclosure is directed to a vector comprising at least one polynucleotide as described herein. Such vectors may be plasmid vectors, viral vectors, vectors for baculovirus expression, transposon based vectors or any other vector suitable for introduction of the polynucleotides described herein into a given organism or genetic background by any means.

Another embodiment of the disclosure is directed to one or more expression vectors comprising the polynucleotides encoding the antibody or binding fragment thereof or antibody mimetic as described herein. The polynucleotide sequences encoding the heavy and light chain variable domains, Fab fragments, or full-length chains of the antibodies disclosed herein are combined with sequences of promoter, translation initiation, 3' untranslated region, polyadenylation, and transcription termination to form one or more expression vector constructs.

In accordance with this embodiment, the expression vector construct encoding the anti-PrP antibody or binding portion thereof can include the nucleic acid encoding the heavy chain polypeptide, a fragment thereof, a variant thereof, or combinations thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region. In some embodiments, the heavy chain polypeptide can include a VH region and a CH1 region. In other embodiments, the heavy chain polypeptide can include a VH region, a CH1 region, a hinge region, a CH2 region, and a CH3 region.

The expression construct can also include a nucleic acid sequence encoding the light chain polypeptide, a fragment thereof, a variant thereof, or combinations thereof. The light chain polypeptide can include a variable light chain (VL) region and/or a constant light chain (CL) region.

The expression construct also typically comprises a promoter sequence suitable for driving expression of the antibody or binding fragment thereof. Suitable promoter sequences include, without limitation, the elongation factor 1-alpha promoter (EF1a) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter. Other promoters suitable for driving gene expression in mammalian cells that are known in the art are also suitable for incorporation into the expression constructs disclosed herein.

The expression construct can further encode a linker sequence. The linker sequence can encode an amino acid sequence that spatially separates and/or links the one or more components of the expression construct (heavy chain and light chain components of the encoded antibody).

Another embodiment of the invention is a host cell comprising the vectors described herein. The antibodies and binding fragments thereof described herein can be optionally produced by a cell line, a mixed cell line, an immortalized cell or clonal population of immortalized cells, as well known in the art (see e.g., Ausubel et al., ed., Current Protocols in Molecular Biology, John Wiley & Sons, Inc., NY, N.Y. (1987-2001); Sambrook et al., Molecular Cloning: A Laboratory Manual, 2$^{nd}$ Edition, Cold Spring Harbor, N.Y. (1989); Harlow and Lane, Antibodies, a Laboratory Manual, Cold Spring Harbor, N.Y. (1989); Colligan et al., eds., Current Protocols in Immunology, John Wiley & Sons, Inc., NY (1994-2001); Colligan et al., Current Protocols in Protein Science, John Wiley & Sons, NY, N.Y., (1997-2001), which are hereby incorporated by reference in their entirety).

The host cell chosen for expression may be of mammalian origin or may be selected from COS-1, COS-7, HEK293, BHK21, CHO, BSC-1, He G2, SP2/0, HeLa, myeloma, lymphoma, yeast, insect, or plant cells, or any derivative, immortalized or transformed cell thereof. Alternatively, the host cell may be selected from a species or organism incapable of glycosylating polypeptides, e.g., a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

The antibodies described herein can be prepared by any of a variety of techniques using the isolated polynucleotides, vectors, and host cells described supra. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. Standard molecular biology techniques are used to prepare the recombinant expression vector, transfect the host cells, select for transformants, culture the host cells and recover the antibody from the culture medium. Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like. Although it is possible to express the antibodies described herein in either prokaryotic or eukaryotic host cells, expression of antibodies in eukaryotic cells is sometimes preferable, and sometimes preferable in mammalian host cells, because such eukaryotic cells (and in particular mammalian cells) are more likely than prokaryotic cells to assemble and secrete a properly folded and immunologically active antibody.

As noted above, exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA*, 77: 4216-4220 (1980), which is hereby incorporated by reference in its entirety). Other suitable mammalian host cells include, without limitation, NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown.

Host cells can also be used to produce functional antibody fragments, such as Fab fragments or scFv molecules. It is understood that variations on the above procedure are within the scope of the present disclosure. For example, it may be desirable to transfect a host cell with DNA encoding functional fragments of either the light chain and/or the heavy chain of an antibody described herein. Recombinant DNA technology may also be used to remove some or all of the DNA encoding either or both of the light and heavy chains that is not necessary for binding to the antigens of interest.

The molecules expressed from such truncated DNA molecules are also encompassed by the antibodies described herein.

The antibodies and antibody binding fragments are recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

In another embodiment, the antibody or binding fragment thereof is a component of a pharmaceutical composition. In one embodiment, the pharmaceutical composition comprises a monoclonal antibody composition. In another embodiment, the pharmaceutical composition comprises one or more different antibodies as described herein. In another embodiment, the pharmaceutical composition comprises one or more antibodies as described herein and one or more prophylactic or therapeutic agents other than the antibodies described herein that are useful for preventing or treating a condition mediated by a toxic protein or peptide oligomers, e.g., Aβ oligomers, Tau oligomers, or PrP oligomers.

The therapeutically effective amount of antibody present in the pharmaceutical composition or formulation is determined by taking into account the desired dose volumes and mode(s) of administration. Exemplary antibody concentrations in the pharmaceutical compositions of the present disclosure include from about 0.1 mg/mL to about 50 mg/mL, from about 0.5 mg/mL to about 25 mg/mL, and from about 2 mg/mL to about 10 mg/mL.

An aqueous formulation is prepared comprising the antibody in a pH-buffered solution. The buffer has a pH in the range from about 4.5 to about 10, from about 5 to about 9, or from about 6 to 8. Examples of buffers include phosphate buffers (e.g., phosphate buffered saline), acetate (e.g. sodium acetate), succinate (such as sodium succinate), gluconate, histidine, citrate and other organic acid buffers.

A polyol, which acts as a tonicifier and may stabilize the antibody, may be included in the formulation. In one embodiment, the tonicifying polyol is a salt such as sodium chloride. In another embodiment, the polyol is a non-reducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, or in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant may also be added to the pharmaceutical composition containing the antibody. Exemplary surfactants include nonionic surfactants such as polysorbates (e.g. polysorbates 20, 80 etc), poloxamers (e.g. poloxamer 188), Pluronic F68, and PEG (polyethylene glycol). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, or from about 0.01% to about 0.1%.

In one embodiment, the pharmaceutical composition contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the pharmaceutical composition, particularly where the formulation is a multi-dose formulation. Suitable preservatives include, without limitation phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. The concentration of preservative may be in the range from about 0.01% to about 5%, from about 0.5% to about 2% and any range or value therein. Non-limiting examples include, no preservative, 0.1-2% m-cresol, 0.1-3% benzyl alcohol, 0.001-0.5% thimerosal, 0.001-2.0% phenol, 0.0005-1.0% alkylparaben(s), and the like. One or more other pharmaceutically acceptable carriers, excipients or stabilizers such as those described in *Remington's Pharmaceutical Sciences* 16th edition, Osol, A. Ed. (1980), which is hereby incorporated by reference in its entirety, may be included in the composition provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions to be used for in vivo administration must be sterile. This is readily accomplished by filtration through sterile filtration membranes, prior to, or following, preparation of the composition.

The pharmaceutical compositions comprising antibodies or binding fragments thereof are for use in, but not limited to, preventing, treating, managing, or ameliorating a condition, or one or more symptoms thereof, mediated by a protein or peptide in a toxic oligomeric form.

In another aspect of the present disclosure the anti-PrP antibodies described herein, binding fragments thereof, or a pharmaceutical composition containing the same, are employed in a method of inhibiting a protein or peptide in a toxic oligomeric form from interacting with prion protein ($PrP^c$) in a subject. This method involves administering to the subject the anti-PrP antibodies described herein, binding fragments thereof, or a pharmaceutical composition containing the same to the subject in an amount effective to inhibit the protein or peptide in its toxic oligomeric form from interacting with $PrP^c$ in the subject.

In another aspect of the present disclosure the anti-PrP antibodies described herein, binding fragments thereof, or a pharmaceutical composition containing the same, are employed in a method of inhibiting onset of one or more symptoms of a condition mediated by a protein or peptide in an oligomeric toxic form in a subject. This method involves administering to the subject the anti-PrP antibodies described herein, binding fragments thereof, or a pharmaceutical composition containing the same in an amount effective to prophylactically inhibit onset of one or more symptoms of the condition mediated by the protein or peptide in its toxic oligomeric form in the subject.

In another aspect of the present disclosure the anti-PrP antibodies described herein, binding fragments thereof, or a pharmaceutical composition containing the same, are employed in a method of treating a condition mediated by a protein or peptide in a toxic oligomeric form in a subject. This method involves administering to the subject the anti-PrP antibodies described herein, binding fragments thereof, or a pharmaceutical composition containing the same in an amount effective to treat the condition mediated by the protein or peptide in its toxic oligomeric form in the subject.

In accordance with these embodiments, proteins or peptides having a toxic oligomeric form include, without limitation amyloid-β, tau, prion, ABri, ADan, and synuclein.

In accordance with these embodiments, conditions mediated by a protein or peptide in a toxic oligomeric form include, without limitation, Alzheimer's disease (AD), Down syndrome (DS), fronto-temporal dementia (FTD), Parkinson's disease (PD), hereditary cerebral hemorrhage with amyloidosis (HCHWA), kuru, Creutzfeldt-Jakob disease (CJD), chronic wasting disease (CWD), Gerstmann-Straussler-Scheinker disease (GSS), Huntington's disease (HD), fatal familial insomnia, British familial dementia, Danish familial dementia, frontotemporal lobar degeneration associated with protein tau (FTLD-tau), frontotemporal lobar degeneration associated with protein FUS (FTLD-FUS), Dementia with Lewy bodies (DLB), Amyotrophic lateral sclerosis (ALS), Mild Cognitive Impairment (MCI), traumatic brain injury (TBI), and chronic traumatic encephalopathy.

In accordance with these embodiments, the "subject" is typically a human, but in some diseases, such as prion protein related diseases, the subject can be a non-human mammal, such as a bovine. Other non-human mammals amenable to treatment in accordance with the methods described herein include, without limitation, primates, dogs, cats, rodents (e.g., mouse, rat, guinea pig), horses, deer, cervids, cattle and cows, sheep, and pigs.

In prophylactic applications, the pharmaceutical compositions of the present invention are administered to a subject that is susceptible to, or otherwise at risk of, a particular condition mediated by a protein or peptide in a toxic oligomeric form, in an amount sufficient to eliminate or reduce the risk of the condition or to delay, inhibit, or prevent the onset of the condition. Prophylactic application also includes the administration of an antibody composition to prevent or delay the recurrence or relapse of a condition mediated by the protein or peptide in its toxic oligomeric form. In the case of Alzheimer's disease, for example, virtually anyone is at risk of suffering from Alzheimer's disease if he or she lives long enough. Therefore, the compositions of the present invention can be administered prophylactically to the general population without the need for any assessment of the risk of the subject patient. The present methods and compositions are especially suitable for prophylactic treatment of individuals who have a known genetic risk of Alzheimer's disease or other condition related to an amyloidogenic protein. Genetic markers associated with a risk of Alzheimer's disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis.

In therapeutic applications, pharmaceutical compositions are administered to a subject suspected of, or already suffering from a condition associated with or caused by a protein or peptide in its toxic oligomeric form in an amount sufficient to cure, or at least partially arrest or alleviate, one or more symptoms of the condition and its complications. An amount adequate to accomplish this is defined as a therapeutically- or pharmaceutically-effective dose. In both prophylactic and therapeutic regimes, agents are usually administered in several dosages until a sufficient response has been achieved. An effective dose of the composition of the present invention, for the treatment of the above described conditions will vary depending upon many different factors, including means of administration, target site, physiological state of the patient, whether the patient is human or an animal, other medications administered, and whether treatment is prophylactic or therapeutic.

In accordance with the prophylactic and therapeutic methods described herein, compositions comprising the antibody or binding fragments thereof are administered in a dosage ranging from about 0.0001 to 100 mg/kg, and more usually 0.01 to 10 mg/kg of the recipient's body weight. For example, the antibody or binding fragment thereof is administered in a dosage of 1, 2, 3, 4, 5, 6, 7, 8, 9 or 10 mg/kg, or higher, for example 15, 20, 25, 30, 35, 40, 45, 50, 55, 60, 65, 70, 75, 80, 85, 90, 95, or 100 mg/kg. An exemplary treatment regime entails administration once per every two weeks or once a month or once every 3 to 6 months. Intervals between single dosages can be weekly, monthly or yearly. Intervals can also be irregular as indicated by measuring blood levels of antibody in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The mode of administration of the antibody, binding fragment thereof, or pharmaceutical composition described herein may be any suitable route that delivers the compositions to the host, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, powder, gel, particle; and/or contained in a syringe, an implanted device, osmotic pump, cartridge, micropump, or other means appreciated by the skilled artisan. Site specific administration may be achieved by, for example, intraarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Administration can be systemic or local. In one embodiment, it may be desirable to administer the antibodies of the invention locally to the area in need of treatment; this may be achieved by, for example, and not by way of limitation, local infusion, by injection, or by means of an implant. A suitable implant being of a porous or non-porous material, including membranes and matrices, such as sialastic membranes, polymers, fibrous matrices (e.g., Tissuel®), or collagen matrices.

In another embodiment, compositions containing the antibody or binding fragment thereof are delivered in a controlled release or sustained release system. In one embodiment, a pump is used to achieve controlled or sustained release. In another embodiment, polymeric materials can be used to achieve controlled or sustained release of the antibody compositions described herein. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation is preferably inert, free of leachable impurities, stable on storage, sterile, and biodegradable. Also, the use of liposomes, microcapsules or microspheres, inclusion complexes, or other types of carriers known in the art are also contemplated.

In yet another embodiment, a controlled or sustained release system can be placed in proximity of the prophylactic or therapeutic target, thus requiring only a fraction of the systemic dose. Controlled and/or release systems for delivery of antibodies known in the art are suitable for use and delivery of compositions containing the antibodies and binding fragments thereof as described herein, see e.g., Song et al, "Antibody Mediated Lung Targeting of Long-Circulating Emulsions," *PDA Journal of Pharmaceutical Science & Technology* 50:372-397 (1995); Cleek et al, "Biodegradable Polymeric Carriers for a bFGF Antibody for Cardiovascular Application," *Pro. Int'l. Symp. Control. Rel. Bioact. Mater.* 24:853-854 (1997); and Lam et al., "Microencapsulation of Recombinant Humanized Monoclonal Antibody for Local Delivery," *Proc. Int'l. Symp. Control Rel. Bioact. Mater.* 24:759-760 (1997), each of which is incorporated herein by reference in their entireties.

In embodiments where the pharmaceutical composition comprises polynucleotides encoding the antibody or binding fragment thereof as described herein, the nucleic acid can be administered in vivo to promote expression of its encoded antibody, by constructing it as part of an appropriate nucleic acid expression vector and administering it so that it becomes intracellular, e.g., by use of a retroviral vector (see e.g., U.S. Pat. No. 4,980,286 to Morgan et al., which is hereby incorporated by reference in its entirety). Alternatively, the nucleic acid can be administered by direct injection, by use of microparticle bombardment (see e.g., a gene gun; Biolistic, Dupont), by coating with lipids or cell-surface receptors or transfecting agents, or by administering it in linkage to a homeobox-like peptide which is known to enter the nucleus (see e.g., Joliot et al, *Proc. Natl. Acad. Sci. USA* 88: 1864-1868 (1991), which is hereby incorporated by reference in its entirety). Alternatively, a nucleic acid can be introduced intracellularly and incorporated within host cell DNA for expression by homologous recombination.

In methods described herein involving intranasal administration of the antibody described herein, the antibody can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges composed of, e.g., gelatin, for use in an inhaler or insufflator may be formulated containing a powder mix of the compound and a suitable powder base such as lactose or starch.

In methods described herein involving oral administration of the antibody described herein, the antibody can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate.

In another embodiment, a pharmaceutical composition comprising a recombinant nucleic acid sequence encoding an antibody or binding portion thereof as described herein, is administered to a subject to facilitate in vivo expression and formation of the antibody for the treatment or prevention of conditions mediated by toxic oligomeric proteins or peptides in a subject. Expression vector constructs suitable for use in this embodiment of the disclosure are described supra.

The polynucleotide compositions can result in the generation of the antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the persistent generation of the antibody in the subject. The composition can result in the generation of the antibody in the subject for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally involve administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

The antibodies, binding fragments thereof, or pharmaceutical compositions containing the same can be packaged in hermetically sealed containers such as an ampoule or sachette indicating the quantity of the antibody or binding fragment thereof. In one embodiment, one or more of the antibodies, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the antibodies or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions of the invention should be stored at between 2° C. and 8° C. in its original container and the antibodies, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions of the invention is supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The antibodies and binding fragments described herein can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Additional surfactants include but are not limited to polysorbate 20 and BRIJ surfactants. The pharmaceutical composition comprising the antibodies described herein prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions (see WO 04/078140 to Bookbinder et al., and U.S. Patent Appl. Publication No. US2006104968 to Bookbinder et al., which are hereby incorporated herein by reference in their entirety).

EXAMPLES

Figures 1A, 1B, 1C, 1D:
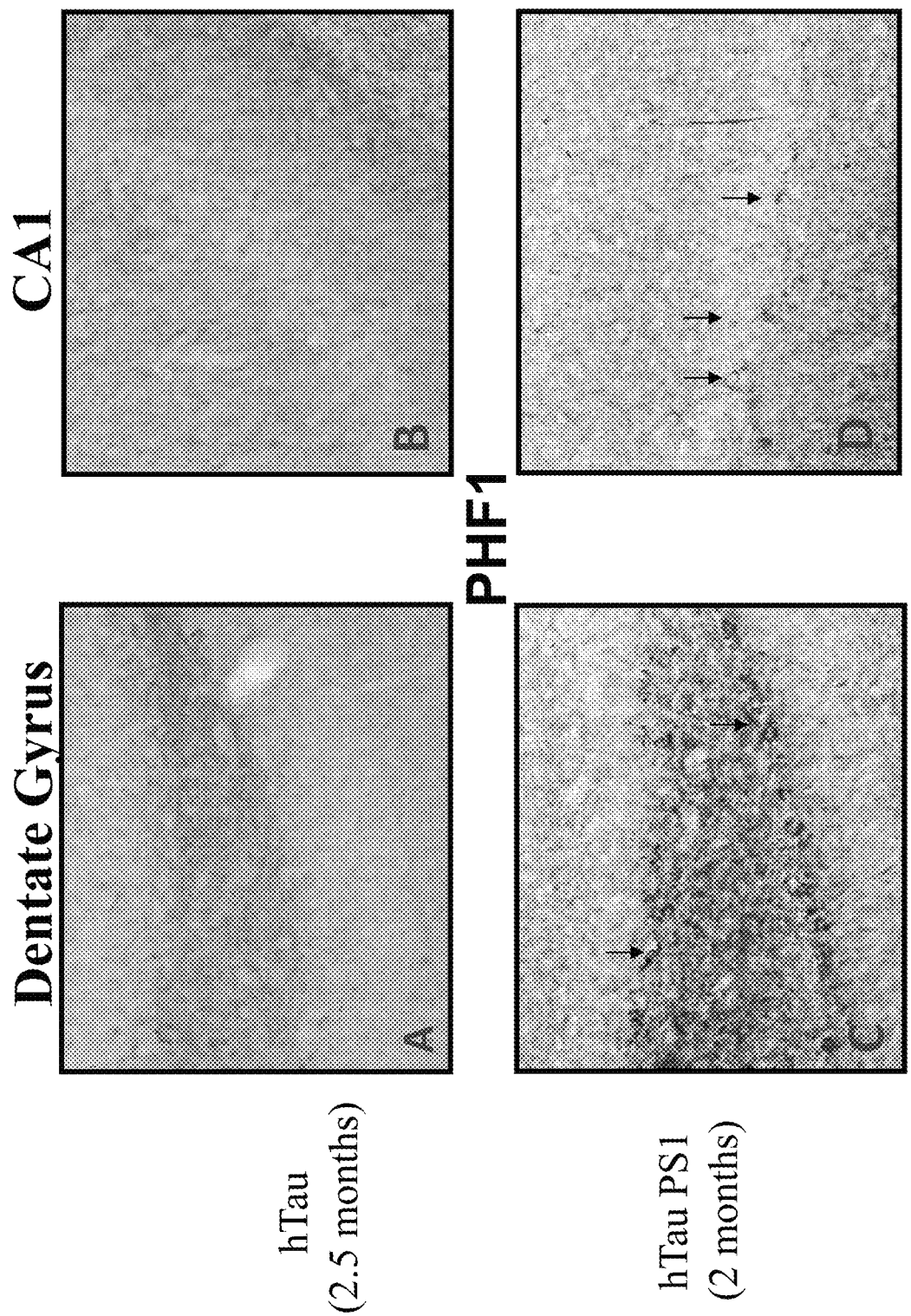
FIGS. 1A-1D show the early development of tau related pathology in the hippocampus of hTau/PS1 transgenic mice in which the anti-PrP antibody described herein was tested.

Examples are provided below to illustrate the present invention. These examples are not meant to constrain the present invention to any particular application or theory of operation Example 1—a Novel Monoclonal Antibody for the Treatment of Conditions Associated with Toxic Oligomeric Proteins or Peptides Recently, a new transgenic model for AD has been generated that expresses mutated PS1 and all human tau isoforms on a murine tau knockout background (hTau/PS1 Tg mice). This model has an earlier onset (at <3 months of age) and more rapid progression of tau pathology than prior htau mouse models (Boutajangout et al., "Passive Immunization Targeting Pathological Phospho-Tau Protein in a Mouse Model Reduces Functional Decline and Clears Tau Aggregates From the Brain," J Neurochem 118:658-667 (2011); Boutajangout et al., "Tau as A Therapeutic Target for Alzheimer's Disease," Curr. Alzheimer Res 8:666-677 (2011), which are hereby incorporated by reference in their entirety). This model is ideally suited for efficient screening of tau-targeting therapy. The early development of PHF1 positive hippocampal neuronal immunolabeling from the age of 2 months in this model is shown in FIGS. 1C and 1D. In models with over expression of just human tau at this age there is no pathology present (See FIGS. 1A and 1B) (Duff et al., "Characterization of Pathology in Transgenic Mice Over-Expressing Human Genomic and cDNA Tau Transgenes," Neurobiol. Dis 7:87-98 (2000), which is hereby incorporated by reference in its entirety). Biochemically the tau pathology in htau/PS1Tg mice is similar to neurofibrillary tangles (NFT) extracted from human AD brains. The similar banding pattern of phosphorylated tau (ptau) in htau/PS1 mice and AD NFT is shown in FIGS. 2B and 2C by immunolabeling with the CP27 antibody, which recognizes phosphorylated tau (Duff et al., "Characterization of Pathology in Transgenic Mice Over-Expressing Human Genomic and cDNA Tau Transgenes," Neurobiol. Dis 7:87-98 (2000), which is hereby incorporated by reference in its entirety). A similar banding pattern of normal human tau is also seen in wild type (WT), AD NFT, and hTau/PS1 brain extracts when immunolabeled with the polyclonal B19 antibody, which recognizes human tau (FIG. 2A) (Boutajangout et al., "Increased Tau Phosphorylation But Absence of Formation of Neurofibrillary Tangles in Mice Double Transgenic for Human Tau and Alzheimer Mutant (M146L) Presenilin-1," Neurosci. Lett 318:29-33 (2002), which is hereby incorporated by reference in its entirety).

The hTau/PS1 Tg model also better resembles Alzheimer's tau pathology in its brain distribution. Clearance of abnormally phosphorylated tau may prevent neuronal cell death in Alzheimer's disease, and the development of active and passive immunization targeting tau pathology has previously been reported (Drummond and Wisniewski, "Alzheimer's Disease: Experimental Models and Reality," Acta Neuropathol 133:155-175 (2017); Boutajangout et al., "Passive Immunization Targeting Pathological Phospho-Tau Protein in a Mouse Model Reduces Functional Decline and Clears Tau Aggregates From the Brain," J Neurochem 118:658-667 (2011); Boutajangout and Wisniewski, "Tau-Based Therapeutic Approaches for Alzheimer's Disease—A Mini-Review," Gerontology 60:381-385 (2014); Boutajangout et al., "Immunotherapy Targeting Pathological Tau Prevents Cognitive Decline in a New Tangle Mouse Model," J Neurosci 30:16559-16566 (2010), which are hereby incorporated by reference in their entirety).

Described herein is a novel monoclonal anti-PrP antibody, referred to as "TW1". The TW1 antibody was raised against a non-denatured PK-resistant fragment of PrP$^{Sc}$ that was purified from brains of CD-1 mice infected with the 139A mouse adapted scrapie agent according to previously published protocols (Kascsak et al., "Immunological Comparison of Scrapie-Associated Fibrils Isolated From Animals Infected With Four Different Scrapie Strains," Journal of Virology 59:676-683 (1986); Carp et al., "Characteristics of Scrapie Isolates Derived From Hay Mites," Journal of Neurovirology 6:137-144 (2000), which are hereby incorporated by reference in their entirety). Wild-type CD-1 mice, two months of age, were immunized subcutaneously with the purified PrP$^{Sc}$ in Freund's adjuvant using a previously published protocol (Sigurdsson et al., "Vaccination Delays the Onset of Prion Disease in Mice," Am. J. Path., 161: 13-17 (2002), which is hereby incorporated by reference in its entirety). Hybridomas were generated as previously described by Spinner et al., "CpG Oligodeoxynucleotide-enhanced Humoral Immune Response and Production of Antibodies to Prion Protein PrPSc in Mice Immunized with 139A Scrapie-associated Fibrils," J. Leukocyte Biol., 14(1): 36-43(2007), which is hereby incorporated by reference in its entirety. TW1 was derived from these hybridomas.

FIG. 3 shows the purification of the cDNA of the heavy chain variable region (VH) and light chain variable region (VL) of anti-PrP TW1. TW1 hybridoma cells were lysed and total RNA was isolated by using Trizol reagent, thereafter, mRNA was purified over a poly (dt) affinity column (FIG. 3). RT-PCR product was sequenced and VH and VL were identified. The amino acid sequences of these regions is provided supra as SEQ ID NO: 4 (VH) and SEQ ID NO: 8 (VL)

The epitope of TW1 is confirmed to be within human Prp residues 94-108. The antibody also binds intact recombinant human PrP. The epitope mapping of TW1 is shown in FIG. 4. FIG. 4 is a dot blot showing TW1 immunoreacting with human PrP sequences PrP 90-108, PrP94-123, and PrP23-231. The TW1 antibody does not recognize the other PrP sequences on the blot. As expected, the TW1 antibody immunolabels PrP$^{Res}$ (protease resistance PrP) from both scrapie and Creutzfeldt-Jakob disease (CJD) (see FIG. 5).

The epitope recognized by TW1 (PrP94-108) is different, but in the same region of PrP bound by the anti-PrP monoclonal (mAb) 6D11. mAb 6D11 is a well characterized anti-PrP mAb that binds an epitope of PrP within residues 97-100 (Pankiewicz et al., "Clearance and Prevention of Prion Infection in Cell Culture by Anti-PrP Antibodies," Eur. J Neurosci 24:2635-2647 (2006); Sadowski et al., "Anti-PrP Mab 6D11 Suppresses PrP$^{Sc}$ Replication in Prion Infected Myeloid Precursor Line FDC-P1/22L and in the Lymphoreticular System In Vivo," Neurobiol Dis 34:267-278 (2009); Spinner et al., "CpG Oligodeoxynucleotide-Enhanced Humoral Immune Response and Production of Antibodies to Prion Protein PrPSc in Mice Immunized With 139A Scrapie-Associated Fibrils," J Leukoc. Biol 14:36-43 (2007), which are hereby incorporated by reference in their entirety). mAb 6D11 has previously been shown to be therapeutically effective against prion infection and also at preventing Aβ toxicity in an AD Tg model with amyloid plaque formation (Sadowski et al., "Anti-PrP Mab 6D11 Suppresses PrP$^{Sc}$ Replication in Prion Infected Myeloid Precursor Line FDC-P1/22L and in the Lymphoreticular System In Vivo," Neurobiol Dis 34:267-278 (2009); Chung et al., "Anti-PrP$^C$ Monoclonal Antibody Infusion as a Novel Treatment for Ab Oligomer Cognitive Cognitive Deficits," BMC Neuroscience 11:130 (2010), which are hereby incorporated by reference in their entirety). The 6D11 mAb was derived from hybridomas using Prnp −/− mice using Titer-Max along with ODN 1826 as an adjuvant (Spinner et al., "CpG Oligodeoxynucleotide-Enhanced Humoral Immune Response and Production of Antibodies to Prion Protein PrPSc in Mice Immunized With 139A Scrapie-Associated Fibrils," *J Leukoc. Biol* 14:36-43 (2007)), whereas TW1 was derived from hybridomas generated from wild-type mice expressing Prnp To test the therapeutic efficacy of mAb TW1, htau/PS1 transgenic (Tg) mice were subject to passive immunization with this mAb by weekly intra-peritoneal injections. The treatment strategy is illustrated in FIG. 6. The efficacy of this antibody was evaluated with behavioral studies as well as by immunohistochemistry and biochemistry studies. As expected, there were no difference between the TW1 treated and vehicle control treated hTau/PS1 mice in motor balance and coordination as tested using the traverse beam (FIG. 7) and rotarod (FIG. 8), or locomotor activity (FIG. 9). However, on novel object testing (FIG. 10), the TW1 treated mice behaved significantly better compared to control treated hTau/PS1 mice. In addition, on a closed field symmetrical maze, TW1 treated mice performed significantly better than control treated hTau/PS1 mice (Day1 one tailed t-test p=0.0001 (FIG. 11A); Day2 one tailed t-test p=0.0008 (FIG. 11B); Day3 one tailed t-test p=0.0001 (FIG. 11C)). The locomotor and behavioral testing was done using previously published methodology (Boutajangout et al., "Immunotherapy Targeting Pathological Tau Prevents Cognitive Decline in a New Tangle Mouse Model," *J Neurosci* 30:16559-16566 (2010); Scholtzova et al., "Innate Immunity Stimulation via Toll-Like Receptor 9 Ameliorates Vascular Amyloid Pathology in Tg-SwDI Mice with Associated Cognitive Benefits," *J Neurosci* 37:936-959 (2017); Boutajangout et al., "Human Umbilical Cord Stem Cell Xenografts Improve Cognitive Decline and Reduce the Amyloid Burden in a Mouse Model of Alzheimer's Disease," *Curr Alzheimer Res* 14:104-111 (2017); Liu et al., "Targeting the Apolipoprotein E/Aβ Interaction by CPO_Aβ17-21P, a Non-Toxic and Non-Fibrillogenic Peptoid, Ameliorates Aβ-Related Pathology and Improves Cognitive Decline in a Mouse Model of Alzheimer's Disease," *Scientific Reports* 7(1):8009 (2017); Boutajangout et al., "Cognitive and Sensorimotor Tasks for Assessing Functional Impairments in Mouse Models of Alzheimer's Disease and Related Disorders," *Methods Mol Biol* 849:529-540 (2012), which are hereby incorporated by reference in their entirety).

Immunohistochemical analysis of PHF1 immunoreactivity using previously published methods (Scholtzova et al., "Innate Immunity Stimulation via Toll-Like Receptor 9 Ameliorates Vascular Amyloid Pathology in Tg-SwDI Mice with Associated Cognitive Benefits," *J Neurosci* 37:936-959 (2017); Boutajangout et al., "Human Umbilical Cord Stem Cell Xenografts Improve Cognitive Decline and Reduce the Amyloid Burden in a Mouse Model of Alzheimer's Disease," *Curr Alzheimer Res* 14:104-111 (2017), which are hereby incorporated by reference in their entirety), showed that the mAb TW1 treated hTau/PS1 Tg mice had a significant reduction in PHF1 immunoreactivity in the motor cortex (FIG. 12A), hippocampus (FIG. 12B), and piriform cortex (FIG. 12C) as compared to vehicle treated hTau/PS1 mice. There was no difference in motor cortex gliosis (FIG. 13A) or dentate gyrus gliosis (FIG. 13B) between mAb TW1 and vehicle treated hTau/PS1 Tg mice as quantitated by GFAP immunoreactivity. These data indicate that mAb TW1 treatment is not associated with any inflammatory toxicity. However, treatment with TW1 reduced the degree of microgliosis as quantitated using Iba1 immunoreactivity (Scholtzova et al., "Innate Immunity Stimulation via Toll-like Receptor 9 Ameliorates Vascular Pathology in Tg-SwDI mice with Associated Cognitive Benefits," *J Neurosci.,* 37(4): 936-959 (2017), which is hereby incorporated by reference in its entirety) in both motor cortex (p=0.04, one-tailed t-test; FIG. 14A) and dendate gyrus (p=0.045, one-tailed t-test; FIG. 14B). TW1 also reduced the levels of pathological tau in the brains of treated mice as assessed using biochemical methods (Goñi et al., "Anti-β-sheet Conformation Monoclonal Reduces Tau and Aβ Oligomer Pathology in an Alzheimer's Model. *Alzheimer's Research and Therapy,* 10:10(2018), which is hereby incorporated by reference in its entirety. Western blot analysis showed that TW1 therapy reduced the ratio of pathological soluble tau to tubulin (PHF1/tubulin) by 40% (p<0.0003) (see FIGS. 15A and 15B).

Hence the results described herein indicate that mAb TW1 is therapeutically active in vivo at reducing AD related pathology with associated cognitive benefits, in the absence of any toxicity. Thus, mAb TW1 will also be therapeutically active in AD, prion diseases, frontotemporal dementia, and traumatic brain injury (TBI)/chronic traumatic encephalopathy (CTE). Normal $PrP^C$ protein expressed on the surface of neurons is a receptor for Aβ oligomers, in part mediating their toxicity (Chung et al., "Anti-$PrP^C$ Monoclonal Antibody Infusion as a Novel Treatment for Ab Oligomer Cognitive Cognitive Deficits," *BMC Neuroscience* 11:130 (2010), which is hereby incorporated by reference in its entirety). Furthermore, $PrP^C$ expression is critical in mediating tau related pathology and neuronal toxicity in the setting of TBI (Rubenstein et al., "Tau Phosphorylation Induced by Severe Closed Head Traumatic Brain Injury is Linked to the Cellular Prion Protein," *Acta Neuropathol Commun* 5:30 (2017), which is hereby incorporated by reference in its entirety). TBI and its associated chronic traumatic encephalopathy (CTE) is now recognized to be a tauopathy related to tau oligomer mediated toxicity (Rubenstein et al., "Tau Phosphorylation Induced by Severe Closed Head Traumatic Brain Injury is Linked to the Cellular Prion Protein," *Acta Neuropathol Commun* 5:30 (2017); McKee et al., "The Neuropathology of Chronic Traumatic Encephalopathy," *Brain Pathol* 25:350-364 (2015), which are hereby incorporated by reference in their entirety). Hence, by binding to $PrP^C$, mAb TW1 inhibits the AP, $PrP^{Sc}$ and tau oligomer interaction with $PrP^C$, thereby reducing the pathology and cognitive deficits associated with AD, prion disease, frontotemporal dementia, and CTE.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An antibody or binding fragment thereof that binds prion protein, said antibody or binding fragment thereof comprising:
   (i) a heavy chain variable region, wherein said heavy chain variable region comprises:
   a complementarity-determining region 1 (H-CDR1) comprising SEQ ID NO: 1;
   a complementarity-determining region 2 (H-CDR2) comprising SEQ ID NO: 2; and
   a complementarity-determining region 3 (H-CDR3) comprising SEQ ID NO: 3 and
   (ii) a light chain variable region, wherein said light chain variable region comprises:
   a complementarity-determining region 1 (L-CDR1) comprising SEQ ID NO: 5;
   a complementarity-determining region 2 (L-CDR2) comprising SEQ ID NO: 6; and
   a complementarity-determining region 3 (L-CDR3) comprising SEQ ID NO: 7.

2. The antibody or binding fragment thereof of claim 1, wherein said antibody or binding fragment binds to human prion protein.

3. The antibody of binding fragment thereof of claim 1, wherein said antibody or binding fragment binds to an epitope of prion protein within or including amino acid residues 94-108 of SEQ ID NO: 9.

4. The antibody or binding fragment thereof of claim 1, wherein said antibody or binding fragment thereof is a monoclonal antibody or binding fragment thereof.

5. The antibody or binding fragment thereof of claim 1, wherein said heavy chain variable region further comprises human or a humanized immunoglobulin heavy chain framework regions.

6. The antibody or binding fragment thereof of claim 5, wherein the heavy chain variable region comprises an amino acid sequence that is at least 80% identical to SEQ ID NO: 4.

7. The antibody or binding fragment thereof of claim 1, wherein said light chain variable region further comprises human or humanized immunoglobulin light chain framework regions.

8. The antibody or binding fragment thereof of claim 7, wherein said light chain variable region comprises an amino acid sequence that is at least 80% identical to SEQ ID NO: 8.

9. The antibody or binding fragment thereof of claim 6 further comprises a light chain variable region, wherein said light chain variable region comprises an amino acid sequence that is at least 85% identical to SEQ ID NO: 8.

10. The antibody or binding fragment thereof of claim 1, wherein said antibody or binding fragment thereof comprises:
    a heavy chain variable region comprising the amino acid sequence of SEQ ID NO: 4 and
    a light chain variable region comprising the amino acid sequence of SEQ ID NO: 8.

11. The antibody or binding fragment thereof of claim 1, wherein said antibody or binding fragment thereof is selected from the group consisting of: a disulfide linked Fv, a scFv, a CDR-grafted antibody, a Fab, a Fab', a F(ab')2, and a Fv.

12. An isolated polynucleotide encoding the antibody or binding fragment thereof of claim 1.

13. A vector comprising the isolated polynucleotide of claim 12.

14. A host cell comprising the vector of claim 13.

15. A pharmaceutical composition comprising:

the antibody or binding fragment thereof of claim 1, and a pharmaceutical carrier.

16. A method of inhibiting a protein or peptide in a toxic oligomeric form from interacting with prion protein ($PrP^c$) in a subject, said method comprising:

administering to the subject the pharmaceutical composition of claim 15, wherein said composition is administered in an amount effective to inhibit the protein or peptide in its toxic oligomeric form from interacting with $PrP^c$ in the subject.

17. The method of claim 16, wherein the protein or peptide in toxic oligomeric form is selected from the group consisting of a tau oligomer, an amyloid beta oligomer, and a prion oligomer.

18. The method of claim 16 further comprising:

selecting a subject having a condition mediated by a protein or peptide in a toxic oligomeric form prior to said administering.

19. The method of claim 18, wherein the condition is selected from the group consisting of Alzheimer's disease (AD). Down syndrome (DS), frontotemporal dementia (FTD), Lewy Body Dementia (LBD), Parkinson's disease (PD), hereditary cerebral hemorrhage with amyloidsis (HCHWA), kuru, Creutzfeldt-Jakob disease (CJD), chronic wasting disease (CWD), Gerstmann-Straussler-Scheinker disease (GSS), bovine spongiform encephalopathy (BSE), ovine Scrapie (Sc), Huntington's disease (HD), fatal familial insomnia, British familial dementia, Danish familial dementia, frontotemporal lobar degeneration associated with protein tau (FTLD-tau), frontotemporal lobar degeneration associated with protein FUS (FTLD-FUS) Amyotrophic lateral sclerosis (ALS), Mild Cognitive Impairment (MCI), traumatic brain injury (TBI), and chronic traumatic encephalopathy.

* * * * *

SEQUENCE LISTING

<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Heavy chain CDR1

<400> SEQUENCE: 1

Glu Asp Tyr Tyr Ile His
1               5

<210> SEQ ID NO 2
<211> LENGTH: 18
<212> TYPE: PRT
<213> ORGANISM: Artificial Sequence
<220> FEATURE:
<223> OTHER INFORMATION: Heavy chain CDR2

<400> SEQUENCE: 2

Trp Ile Gly Arg Ile Asp Pro Glu Asp Asp Glu Thr Lys Tyr Ala Pro
1               5                   10                  15

Lys Phe

<210> SEQ ID NO 3
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 3

Arg Phe Asp Gly Ile Gly Asp Tyr Ser Asp Ser
1               5                   10

<210> SEQ ID NO 4
<211> LENGTH: 108
<212> TYPE: PRT
<213> ORGANISM: Artificial Sequence
<220> FEATURE:
<223> OTHER INFORMATION: Heavy chain variable region

<400> SEQUENCE: 4

Met Gln Glu Ser Gly Ala Glu Leu Val Lys Pro Gly Ala Ser Val Lys
1               5                   10                  15

Leu Ser Cys Thr Val Ala Gly Phe Asn Ile Glu Asp Tyr Tyr Ile His
            20                  25                  30

Trp Val Lys Gln Arg Pro Glu Gln Gly Leu Glu Trp Ile Gly Arg Ile
        35                  40                  45

Asp Pro Glu Asp Asp Glu Thr Lys Tyr Ala Pro Lys Phe Leu Gly Lys
    50                  55                  60

Ala Thr Val Thr Ser Asp Thr Ser Asn Thr Val Phe Leu Gln Leu
65                  70                  75                  80

Arg Ser Leu Thr Ser Glu Asp Thr Ala Ile Tyr Tyr Cys Gly Arg Phe
                85                  90                  95

Asp Gly Ile Gly Asp Tyr Ser Asp Ser Trp Gly Gln
            100                 105

<210> SEQ ID NO 5
<211> LENGTH: 8
<212> TYPE: PRT
<213> ORGANISM: Artificial Sequence
<220> FEATURE:
<223> OTHER INFORMATION: Light chain CDR1

<400> SEQUENCE: 5

Ser Leu Leu Ala Ser Asp Glu Gln
1               5

<210> SEQ ID NO 6
<211> LENGTH: 10
<212> TYPE: PRT
<213> ORGANISM: Artificial Sequence
<220> FEATURE:
<223> OTHER INFORMATION: Light chain CDR2

<400> SEQUENCE: 6

Leu Met Tyr Leu Gly Ser Lys Leu Asp Ser
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Light chain CDR3

<400> SEQUENCE: 7

Trp Gln Gly Thr His Phe Pro Gln Thr
1               5

<210> SEQ ID NO 8
<211> LENGTH: 98
<212> TYPE: PRT
<213> ORGANISM: Artificial Sequence
<220> FEATURE:
<223> OTHER INFORMATION: Light chain variable region

<400> SEQUENCE: 8

Ala His Ser Val Ser Ile Ser Cys Lys Ser Ser Gln Ser Leu Leu Ala
1               5                   10                  15

Ser Asp Glu Gln Thr Tyr Leu Asn Trp Leu Leu Gln Arg Pro Gly Gln
                20                  25                  30

Ser Pro Lys Arg Leu Met Tyr Leu Gly Ser Lys Leu Asp Ser Gly Val
            35                  40                  45

Pro Asp Arg Phe Thr Gly Cys Gly Ser Gly Thr Asp Phe Thr Leu Lys
        50                  55                  60

Ile Ser Arg Val Glu Ala Glu Asp Leu Gly Val Tyr Tyr Cys Trp Gln
65                  70                  75                  80

Gly Thr His Phe Pro Gln Thr Phe Gly Gly Gly Thr Lys Leu Glu Ile
                85                  90                  95

Lys Arg

<210> SEQ ID NO 9
<211> LENGTH: 253
<212> TYPE: PRT
<213> ORGANISM: Homo sapien

<400> SEQUENCE: 9

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg

-continued

```
                35                  40                  45
Tyr Pro Pro Gln Gly Gly Gly Trp Gly Gln Pro His Gly Gly Gly
        50                  55                  60

Trp Gly Gln Pro His Gly Gly Trp Gly Gln Pro His Gly Gly Gly
65                  70                  75                  80

Trp Gly Gln Pro His Gly Gly Trp Gly Gln Gly Gly Gly Thr His
                85                  90                  95

Ser Gln Trp Asn Lys Pro Ser Lys Pro Lys Thr Asn Met Lys His Met
                100                 105                 110

Ala Gly Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```